United States Patent [19]

Takaya et al.

[11] Patent Number: 5,530,150
[45] Date of Patent: Jun. 25, 1996

[54] PHOSPHINE COMPOUND, COMPLEX CONTAINING THE PHOSPHINE COMPOUND AS LIGAND, PROCESS FOR PRODUCING OPTICALLY ACTIVE ALDEHYDE USING THE PHOSPHINE COMPOUND OR THE COMPLEX, AND 4-[(R)-1'-FORMYLETHYL]AZETIDIN-2-ONE DERIVATIVES

[75] Inventors: Hidemasa Takaya, Kusatsu; Nozomu Sakai, Kobe; Kyoko Tamao, Kyoto; Satoshi Mano, Ichinomiya; Hidenori Kumobayashi, Kanagawa; Tetsuo Tomita, Tokyo; Takao Saito, Kanagawa; Kazuhiko Matsumura, Kanagawa; Yasushi Kato, Kanagawa; Noboru Sayo, Kanagawa, all of Japan

[73] Assignee: Takasago International Corporation, Tokyo, Japan

[21] Appl. No.: 323,492

[22] Filed: Oct. 12, 1994

Related U.S. Application Data

[63] Continuation-in-part of Ser. No. 209,069, Mar. 11, 1994, abandoned, and a continuation-in-part of Ser. No. 209,070, Mar. 11, 1994, abandoned, and a continuation-in-part of Ser. No. 208,378, Mar. 10, 1994, abandoned, and a continuation-in-part of Ser. No. 209,051, Mar. 11, 1994, abandoned.

[30] Foreign Application Priority Data

| Mar. 12, 1993 | [JP] | Japan | 5-52538 |
| Mar. 12, 1993 | [JP] | Japan | 5-52539 |
| Mar. 12, 1993 | [JP] | Japan | 5-52540 |
| Mar. 12, 1993 | [JP] | Japan | 5-77484 |

[51] Int. Cl.$^6$ ............... C07F 15/00; C07F 9/02
[52] U.S. Cl. ............... 556/18; 556/21; 556/136; 568/14; 568/17; 568/423; 558/73; 558/74; 558/218
[58] Field of Search ............... 556/18, 21, 136; 568/14, 17, 423; 558/73, 74, 218

[56] References Cited

PUBLICATIONS

Sakai et al., J. Am. Chem. Soc., vol. 115, No. 15, pp. 7033–7034 (1993).

*Primary Examiner*—Porfirio Nazario-Gonzales
*Attorney, Agent, or Firm*—Oblon, Spivak, McClelland, Maier & Neustadt

[57] ABSTRACT

A phosphine compound represented by one of the formulas:

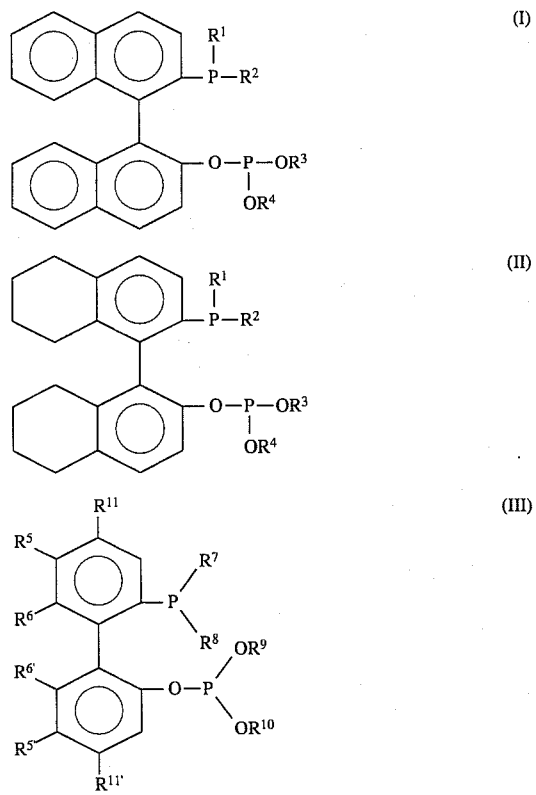

wherein $R^1$ and $R^2$, which may be the same or different, each represent a phenyl group or a phenyl group substituted with a halogen atom or a lower alkyl group or taken together form a divalent hydrocarbon group; and $R^3$ and $R^4$, which may be the same or different, each represent a lower alkyl group, a phenyl group or a phenyl group substituted with a halogen atom, a lower alkyl group or a lower alkoxy group or taken together form a divalent hydrocarbon group, and wherein $R^6$ and $R^{6'}$ which may be the same or different, each represent a hydrogen atom, a lower alkyl group or a lower alkoxy group; $R^5$, $R^{5'}$, $R^{11}$ and $R^{11'}$ which may be the same or different, each represent a hydrogen atom, a lower alkyl group, a lower alkoxy group or a halogen atom; or a pair of $R^5$ and $R^6$ or a pair of $R^{5'}$ and $R^{6'}$ may form a ring; $R^7$ and $R^8$, which may be the same or different, each represent a phenyl group or a phenyl group substituted with a lower alkyl group, a halogen atom or a lower alkoxy group; and $R^9$ and $R^{10}$, which may be the same or different, each represent a phenyl group or a phenyl group substituted with a lower alkyl group, a lower alkoxy group or a halogen atom; or $R^9$ and $R^{10}$ may be taken together to form a divalent hydrocarbon group.

11 Claims, No Drawings

PHOSPHINE COMPOUND, COMPLEX CONTAINING THE PHOSPHINE COMPOUND AS LIGAND, PROCESS FOR PRODUCING OPTICALLY ACTIVE ALDEHYDE USING THE PHOSPHINE COMPOUND OR THE COMPLEX, AND 4-[(R)-1'-FORMYLETHYL]AZETIDIN-2-ONE DERIVATIVES

CROSS REFERENCE TO RELATED APPLICATIONS

This application is a continuation-in-part of application Ser. No. 08/209,069 filed Mar. 11, 1994, now abandoned; application Ser. No. 08/209,070 filed Mar. 11, 1994, now abandoned; application Ser. No. 08/208,378 filed Mar. 10, 1994, now abandoned; and application Ser. No. 08/209,051 filed Mar. 11, 1994, now abandoned.

SUMMARY OF THE INVENTION

1. Field of the Invention

The present invention relates to a phosphine compound and a transition metal complex which contains this compound as a ligand and is useful as a catalyst for a variety of asymmetric synthetic reactions.

This invention also relates to a novel phosphine compound and, more particularly, to a phosphine compound serving as a useful catalyst for asymmetric hydroformylation when combined with a transition metal, e.g., rhodium; to a process for producing an optically active aldehyde using a combination of the phosphine compound and a transition metal; to a process for producing an intermediate for carbapenem antibiotics using a combination of the phosphine compound and a transition metal; and to the resulting intermediate.

Further, the present invention relates to a process for producing optically active aldehydes, and more particularly to a process for producing an optically active aldehyde represented by formula (B) using a vinyl compound represented by formula (A), carbon monoxide and hydrogen as starting materials.

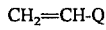  (A)

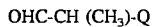  (B)

wherein Q is as defined infra.

2. Description of the Background

Many transition metal complexes have heretofore been used as catalysts for synthetic organic reactions. In particular, noble metal complexes are expensive, but safe and easy to handle, and so many synthetic methods make use of them as catalysts. There are a great number of reports of synthetic organic reactions which have not been feasible by previous methods or processes that are now possible with transition metal complex catalysts.

Among others, complexes obtained by coordinating an optically active tertiary phosphine to a transition metal such as rhodium, palladium, ruthenium or nickel often have excellent performance as catalysts for asymmetric synthetic reactions. In order to enhance the performance of these catalysts, a number of phosphine compounds having a special structure have been developed to date ["Organometallic Chemistry" Kagaku Sosetsu (The Elements of Chemistry), 32, edited by The Chemical Society of Japan, 237–238 (1982)].

Asymmetric hydroformylation reactions have heretofore attracted much attention in the field of synthetic organic chemistry because of their good practical utility for the synthesis of optically active aldehydes. In particular, in order to achieve both high regioselectivity (ratio of branched chain to linear chain) and high stereoselectivity in a step wherein a carbon-carbon bond is formed, a great deal of effort has been given to the development of an effective catalyst for asymmetric synthesis. For example, rhodium or platinum complexes modified by an optically active diphosphine have been used as catalysts.

However, results obtained to date have been not satisfactory in many cases from the viewpoint of synthetic chemistry. When the platinum catalyst is used in an asymmetric hydroformylation reaction, its reaction rate is generally slow, and besides there is a tendency for the hydrogenation reaction of a starting material to competitively progress. The use of the rhodium catalyst solves such drawbacks. However, such a catalyst is not entirely without problems.

There have been several attempts to asymmetrically hydroformylate vinyl acetate to obtain optically active 2-acetoxypropanal. For example, according to C. F. Hobbs and W. S. Knowles, J. Org. Chem., 46, 4422 (1981), vinyl acetate is asymmetrically hydroformylated using a mixture of DIPHOL and Rh(cod)(acac) as a catalyst to achieve an optical purity of 51% ee at the highest. The reference discloses 2,3-0-isopropylidene- 2,3-dihydroxy-1,4-bis-(diphenylphosphino)butane as a phosphine ligand.

The present inventors effected an asymmetric hydroformylation reaction of vinyl acetate using a rhodium catalyst containing, as a ligand, bis(triarylphosphite) which is easier to synthesize than DIPHOL and reported it in Tetrahedron Asymmetry, 3(5), 583–586 (1992). This publication describes the optically phosphine 2,2'-bis(diphenylphosphino)- 1,1'-binaphthyl (BINAP) and a rhodium complex prepared from this phosphine. According to this process, practical utility in industry was greatly improved, but its optical purity was 49% ee and hence differed little from that of the conventional process.

Besides, an example of the asymmetric hydroformylation reaction of olefins making use of a rhodium complex containing an optically active bidentate phosphine (DIOP or the like) as a ligand is described in Bull. Chem. Soc. Japan, 52, 2605–2608 (1979), and an example of the asymmetric hydroformylation reaction of methyl α-acetamidoacrylate making use of a rhodium complex containing an optically active bidentate phosphine as a ligand is described in Tetrahedron Asymmetry, 10, 693 (1990). In each case, the optical purity is not high.

In the hydroformylation reaction, good yield can be generally achieved using a cobalt or rhodium catalyst. However, various means have been made for enhancing the selectivity of a position to which a formyl group adds. The positional selectivity has become very high by methods such as the addition of a phosphine ligand. However, it has been difficult to furthermore stereospecifically control the hydroformylation, and the optical purity of an aldehyde produced has been up to 50% ee at most.

In order to enhance steric selectivity, it is necessary to strictly control the configuration space about a central metal of a catalyst, thereby limiting the route of the addition of the formyl group in one direction on the configuration space. Such control of the configuration space can be attained only by satisfactorily designing the steric configuration of the ligand. It is apparent that the catalysts conventionally used are insufficient in controlling the configuration space. It is therefore desirable to design a ligand which uses an optically active binaphthol which has excellent asymmetry source and which is readily available. For such an end, bis(triarylphosphite) ligands have already been synthesized and tested. However, unsatisfactory results have only been obtained.

U.S. Pat. No. 4,206,399 discloses 2,2'-bis(diphenylphosphino)- 5,5',6,6', 7,7',8,8'-octahydro-1,1'-binaphthyl and asymmetric hydrogenation using a transition metal complex containing the phosphine as a ligand.

A great number of special phosphine compounds have thus been developed for the purpose of providing a catalyst having higher performance in asymmetric syntheses. However, they are not always satisfactory in selectivity, conversion, catalytic activity, asymmetric yield, and the like depending on the substrate or the reaction to which they are applied.

In another field of endeavor, carbapenem antibiotics have recently undergone marked development,an example of which is the preparation of 4-[(R)-1'-carboxyethyl]azetidin-2-one derivatives of formula (III)

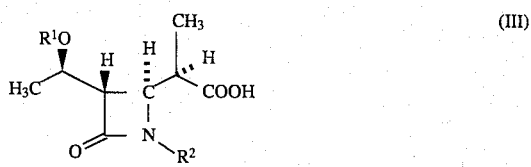

wherein $R^1$ represents a hydrogen atom or a hydroxyl-protecting group; and $R^2$ represents a hydrogen atom or an amino-protecting group. These derivatives are important intermediates for carbapenem antibiotics and have been given extensive study.

The carbapenem antibiotics having no substituent at the 1-position of the carbapenem skeleton are chemically unstable at high concentrations and are readily metabolized by renal dehydropeptidase. It is known that introduction of an alkyl group in the β-configuration of the molecule at the 1-position provides a compound which has increased stability against renal dehydropeptidase and therefore can be used alone and not in combination with a renal dehydropeptidase inhibitor.

A number of reports have been made on synthesis of the compound of formula (III). In particular, processes comprising nucleophilic substitution at the 4-position of a 4-acetoxyazetidin-2-one derivative represented by formula (IV)

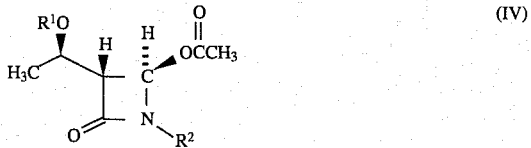

wherein $R^1$ and $R^2$ are as defined above, by means of various nucleophiles are known.

Other known processes for synthesizing the intermediate compound (III) include a process comprising alkylation of a compound represented by formula (V):

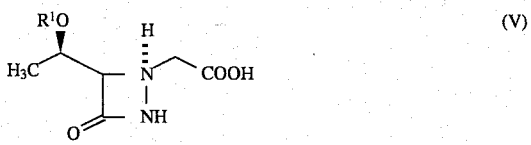

wherein $R^1$ is as defined above, with lithium diisopropylamide and a process comprising catalytic hydrogenation of the exomethylene group of a compound represented by formula (VI):

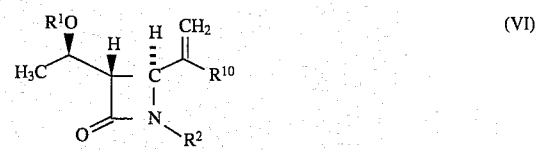

wherein $R^1$ and $R^2$ are as defined above; and $R^{10}$ represents an alkyl group, a carboxyl group or an alkoxycarbonyl group, or asymmetric hydrogenation of the exo-methylene group of the compound of formula (VI) in the presence of a specific catalyst.

The compounds obtained from the intermediates (III) as produced by the above-mentioned processes are, in most cases, mixtures of stereoisomers, i.e., an α-isomer and a β-isomer, at a specific ratio.

As stated above, a number of special phosphine compounds have so far been prepared in order to get an active catalyst for asymmetric hydroformylation. However, the known phosphine complex catalysts are not always satisfactory in terms of regio and enantio selectivities. There has therefore been a demand to develop a novel phosphine compound and a transition metal-phosphine complex performing higher regio and enantio selectivities in comparison to conventional catalysts.

There has also been a demand to develop an efficient process for producing a compound (III) having a methyl group in the β-configuration, which is a versatide as an intermediate for carbapenem antibiotics, or a precursor thereof.

SUMMARY OF THE INVENTION

As described above, many particular phosphine compounds have heretofore been developed for providing catalysts having higher performance as catalysts for asymmetric synthetic reactions. These compounds are not always fully satisfactory from the viewpoint of selectivity, conversion, catalytic activity, optical purity and the like though may vary according to the substrate and reaction intended. It is therefore an object of the present invention to provide a phosphine compound which permits the provision of complexes having high catalytic ability compared with the conventionally-known catalysts.

In has now been found that a transition metal complex containing, as a ligand, a phosphine compound having an optically active binaphthyl skeleton is remarkably superior in optical purity and selectivity in asymmetric synthesis to the conventionally-known optically active phosphine-transition metal complexes, thus leading to completion of the present invention. When this complex is used to conduct the hydroformylation of various vinyl compounds, a high degree of stereoselective synthesis is achieved which is unexpected from what is known about conventional catalysts.

In an aspect of the present invention, there is thus provided a phosphine compound represented by the following formula (I):

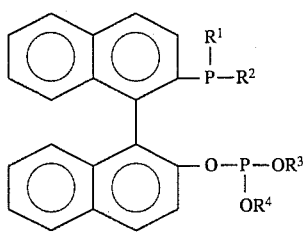

(I)

wherein $R^1$ and $R^2$ are identical with or different from each other and mean individually a phenyl group which may be substituted by a halogen atom or lower alkyl group, or denote together a divalent hydrocarbon group, $R^3$ and $R^4$ are identical with or different from each other and mean individually a lower alkyl group or a phenyl group which may be substituted by a halogen atom, lower alkyl group or lower alkoxy group, or denote together a divalent hydrocarbon group.

In another aspect of the present invention, there is also provided a transition metal-phosphine complex containing, as a ligand, the phosphine compound as described above.

In a further aspect of the present invention, there is provided a rhodium-phosphine complex represented by the following formula (2-a) or (2-b):

[Rh(L) (Y) (X)]          (2-a)

[Rh(L) (Y) (X)          (2-b)

wherein L means the phosphine compound (I) as described above, Y denotes carbon monoxide, a monodentate or bidentate neutral ligand having lower coordinating strength than that of carbon monoxide, olefin or diene, and X stands for a hydrogen atom, monovalent anion or triphenylphosphine, or X and Y mean together a β-diketonate.

When the transition metal-phosphine complex as described supra is used as a catalyst for asymmetric synthesis, a product having the intended absolute configuration can be obtained in a high optical purity at a high yield.

In an aspect of the present invention, an optically active aldehyde represented by formula (B):

OHC-CH (CH₃)-Q          (B)

wherein Q means a halogen atom, lower alkyl group, phthalimide group, lower alkylcarbonyloxy group, cyano group, carboxyl group, lower alkyloxycarbonyl group, lower alkoxy group, lower alkylcarbonyl group, acetylamino group, benzoylamino group, monoalkylamino group, dialkylamino group, benzoyl group, phenyl group which may be substituted by a halogen atom, lower alkyl group or lower alkoxy group, or naphthyl group which may be substituted by a halogen atom, lower alkyl group or lower alkoxy group is produced by a process comprising hydroformylating a vinyl compound represented by the following formula (A):

CH₂=CH-Q          (A)

wherein Q has the same meaning as defined above, using, as a catalyst, a rhodium-phosphine complex represented by the formula (2-a) or (2-b) supra. An optically active aldehyde is synthesized in high yield at high optical quality and at low cost.

Still another aspect of the invention is a transition metal complex containing a novel phosphine compound having a 5,5',6,6',7,7',8,8'-octahydro-1,1'-binaphthyl skeleton (i.e., bitetrahydronaphthalene group). This compound having a phosphine structure and a phosphite structure in one molecule is considerably superior to the known optically active phosphine-transition metal complexes in asymmetric yield and selectivity in asymmetric syntheses. The compound has the structure (II):

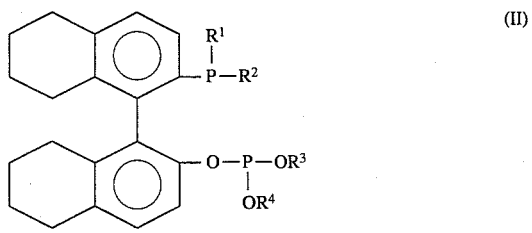

(II)

wherein $R^1$ and $R^2$ which may be the same or different, each represent a phenyl group or a phenyl group substituted with a halogen atom or a lower alkyl group or they are taken together to form a divalent hydrocarbon group; and $R^3$ and $R^4$, which may be the same or different, each represent a lower alkyl group, a phenyl group or a phenyl group substituted with a halogen atom, a lower alkyl group or a lower alkoxy group or they are taken together to form a divalent hydrocarbon group.

A transition metal-phosphine complex containing the phosphine compound of formula (II) as a ligand is also an aspect of the invention.

Still another aspect of the present invention is a phosphine compound represented by formula (VII):

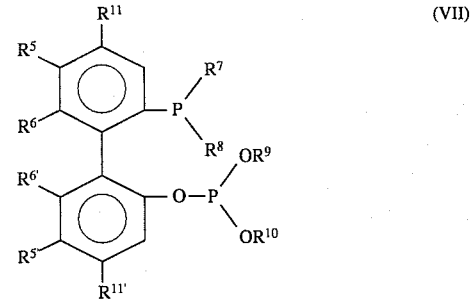

(VII)

wherein $R^6$ and $R^{6'}$, which may be the same or different, each represent a hydrogen atom, a lower alkyl group or a lower alkoxy group; $R^5$, $R^{5'}$, $R^{11}$, and $R^{11'}$, which may be the same or different, each represent a hydrogen atom, a lower alkyl group, a lower alkoxy group or a halogen atom; or a pair of $R^5$ and $R^6$ or a pair of $R^{5'}$ and $R^{6'}$ may form a ring; $R^7$ and $R^8$ which may be the same or different, each represent a phenyl group or a phenyl group substituted with a lower alkyl group, a halogen atom or a lower alkoxy group; and $R^9$ and $R^{10}$, which may be the same or different, each represent a phenyl group or a phenyl group substituted with a lower alkyl group, a lower alkoxy group or a halogen atom; or $R^9$ and $R^{10}$ may be taken together to form a divalent hydrocarbon group.

The present invention further relates to a phosphine compound represented by formula (VIII):

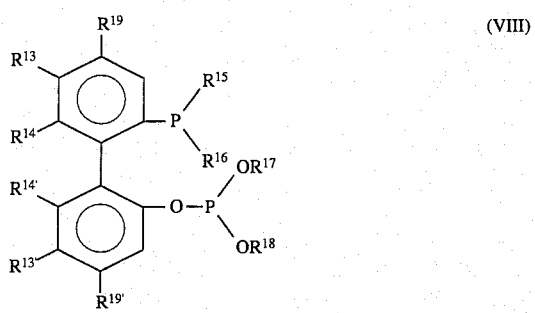

(VIII)

wherein $R^{14}$ and $R^{14'}$, which may be the same or different, each represent a hydrogen atom, a lower alkyl group or a lower alkoxy group; $R^{13}$, $R^{13'}$, $R^{19}$ and $R^{19'}$, which may be the same or different, each represent a hydrogen atom, a lower alkyl group, a lower alkoxy group or a halogen atom; $R^{15}$ and $R^{16}$, which may be the same or different, each represent a phenyl group or a phenyl group substituted with a lower alkyl group, a halogen atom or a lower alkoxy group; and $R^{17}$ and $R^{18}$, which may be the same or different, each represent a phenyl group or a phenyl group substituted with a lower alkyl group, a lower alkoxy group or a halogen atom; or $R^{17}$ and $R^{18}$ may be taken together to form a divalent hydrocarbon group.

The present invention further relates to a transition metal-phosphine complex having the phosphine compound represented by formula (VII) as a ligand.

The present invention furthermore relates to a process for producing an optically active aldehyde comprising hydroformylation of an olefin represented by formula (IX):

$$Q_1\text{-CH}=\text{CH-}Q_2 \qquad (IX)$$

wherein $Q_1$ represents a hydrogen atom or a lower alkyl group; and $Q_2$ represents a lower alkyl group, a lower alkoxy group, a halogen atom, a lower alkylcarbonyloxy group, a cyano group, a carboxyl group, a lower alkylcarbonyl group, a lower alkoxycarbonyl group, a phthalimido group, an acetylamino group, a benzoylamino group, a mono-lower-alkylamino group, a di-lower-alkylamino group, a benzoyl group, a phenyl group, a naphthyl group, a phenyl or naphthyl group substituted with a lower alkyl group, a lower alkoxy group or a halogen atom, or a group represented by formula (X):

(X)

wherein $R^{20}$ represents a hydrogen atom or a hydroxyl-protecting group; or $Q_1$ and $Q_2$ may be taken together to form a ring represented by formula (XI):

(XI)

wherein n represents 1 or 2, in the presence of a complex of the phosphine compound of formula (VII) and a transition metal, e.g., rhodium, or both of the phosphine compound of formula (VII) and a transition metal compound as a catalyst.

The present invention also relates to a 4-[(R)-1'-formyl-ethyl]azetidin-2-one derivative represented by formula (XII):

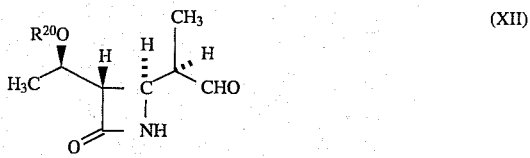

(XII)

wherein $R^{20}$ is as defined above, which is obtained by utilizing the above-mentioned hydroformylation.

DETAILED DESCRIPTION OF THE PREFERRED EMBODIMENTS

In all of the compounds of the invention, the term "lower alkyl group" means a linear or branched alkyl group having 1–6 carbon atoms including methyl, ethyl, propyl, isopropyl, butyl, isobutyl, sec-butyl, tert-butyl, pentyl or hexyl group. The term "halogen atom" means a chlorine, bromine, iodine or fluorine atom, while the term "lower alkoxy group" means a linear or branched alkoxy group having 1–6 carbon atoms, such as a methoxy, ethoxy, propoxy, isopropoxy, butoxy, isobutoxy, sec-butoxy or tert-butoxy group. The lower alkyl groups in the lower alkylcarbonyloxy group, lower alkyloxycarbonyl group and lower alkylcarbonyl group also have the same meaning as described above. Further, the alkyl groups in the monoalkylamino group and dialkylamino group also have the same meaning as described above.

Besides, the term "divalent hydrocarbon group" as used herein means a biarylene group such as a biphenyl group which may have a substituent group, a binaphthyl group which may have a substituent group, a biphenanthryl group which may have a substituent group or a bianthryl group which may have a substituent group, or a linear or branched, saturated or unsaturated alkylene group having 2–7 carbon atoms, such as an ethylene, trimethylene, tetramethylene, pentamethylene, 1,4-dimethyltetramethylene, 1,3-butadienylene or 1,4-dimethyl-1,3-butadienylene group. Examples of the substituent group substitutable on the bisarylene group include lower alkyl groups, halogen atoms and lower alkoxy groups.

As examples of the transition metal, may be mentioned rhodium, ruthenium, palladium, iridium, platinum, cobalt, nickel, titanium and the like. Rhodium, ruthenium, iridium and palladium are particularly preferred for the formation of complexes with the phosphine of formula II. A rhodium-phosphine complex where the transition metal is rhodium is represented by the following formula (2-a) or (2-b):

[Rh(L) (Y) (X)]  (2-a)

[Rh(L) (Y)](X)  (2-b)

wherein L means the phosphine compound according to this invention, Y denotes carbon monoxide, a monodentate or bidentate neutral ligand having lower coordinating strength than that of carbon monoxide, olefin or diene, and X stands for a hydrogen atom, monovalent anion or triphenylphosphine, or X and Y mean together a β-diketonate.

The phosphine compound (I) of the present invention is prepared in accordance with, for example, a process represented by the following reaction scheme:

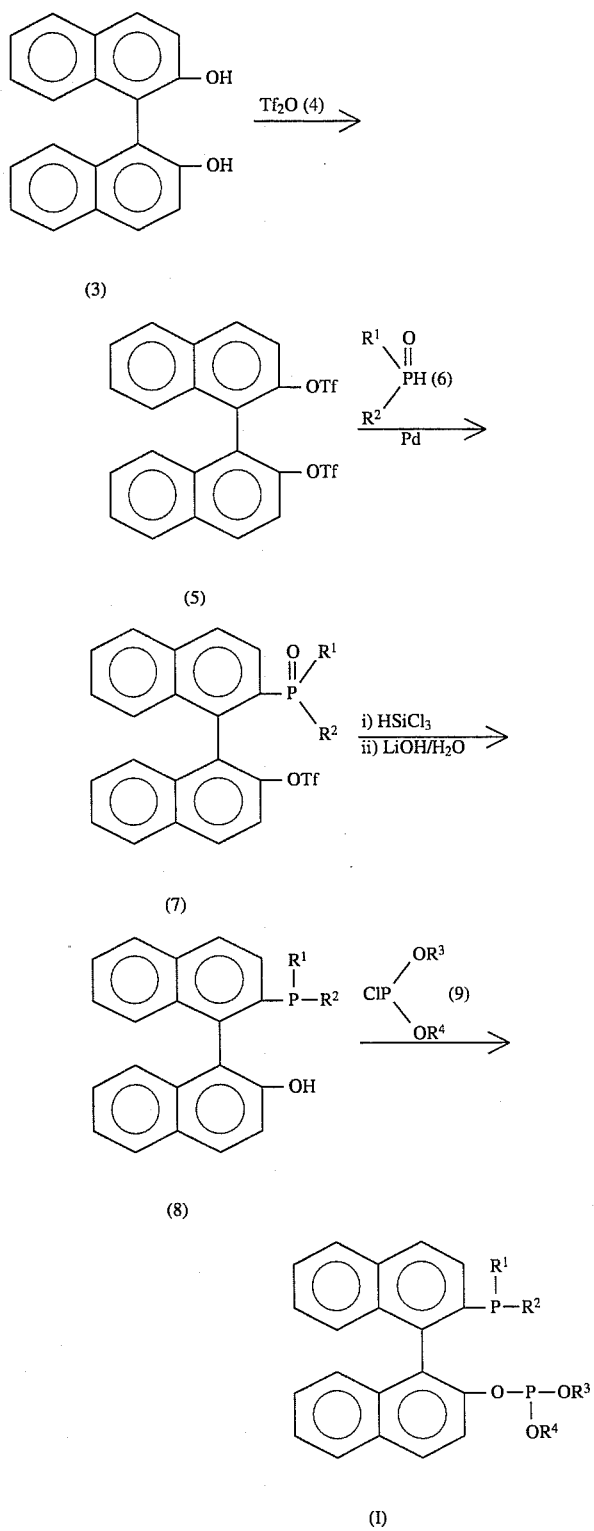

wherein Tf means a trifluoromethanesulfonyl group, and $R^1$, $R^2$, $R^3$ and $R^4$ have the same meaning as defined above.

More specifically, following Tetrahedron Letters, 31, 6321–6324 (1990), trifluoromethanesulfonic anhydride (4) is reacted with 1,1-bi-2-naphthol (3) to form 2,2'-bis(trifluoromethanesulfonyloxy)- 1,1'-binaphthyl (5). This compound (5) is reacted with phosphine oxide (6) in the presence of a palladium catalyst to form 2-phosphinyl-2'-trifluoromethanesulfonyloxy- 1,1'-binaphthyl (7). Compound (7) is then reduced in the presence of triethylamine, followed by hydrolysis of the reduction product to form 2-phosphino-2'-hydroxy- 1,1'-binaphthyl (8). Further, this compound (8) is reacted with chlorophosphine (9) in the presence of triethylamine, whereby the phosphine compound (I) of the present invention is prepared.

The optically active 1,1'-bi-2-naphthol used as a starting material in the present invention can be easily synthesized in a high optical purity at a high yield in accordance with the process disclosed in J. Org. Chem., 53, 3607 (1988) and Japanese Patent Application Laid-Open No. 13063/1989. More specifically, it is synthesized by forming a clathrate complex only from optically active 0,0'-dimethyl-N,N'-tetramethyltartaric amide synthesized using natural or synthetic tartaric acid as a raw material and one of optically active substances of racemic binaphthol, and then decomposing the clathrate complex.

Besides, the transition metal-phosphine complex (2) according to the present invention can be prepared in accordance with any known method. A description will hereinafter be made taking the case of rhodium.

For example, $[Rh(COD)_2]ClO_4$ prepared from $[Rh(COD)(Cl)]_2$ (COD: 1,5-cyclooctadiene) and $AgClO_4$ in accordance with the process described in J. Am. Chem. Soc., 93, 3089 (1971) is reacted with the phosphine compound (I) (L) according to the present invention, thereby obtaining $[Rh(L)(COD)]ClO_4$.

Further, [Rh(L)(CO)Cl] is obtained by reacting the phosphine compound (I) of this invention with commercially-available $[Rh(CO)_2Cl]_2$ at room temperature in methylene chloride in accordance with the process described in Inorg. Synth., 8, 214–217 (1966).

For the binaphthyl skeleton of the phosphine compound (I) according to the present invention, optically active substances and racemic modification exist. All the compounds are embraced in the scope of the present invention.

In this invention, examples of the rhodium-phosphine complex include the following compounds. In the following compounds, L and COD have the same meaning as defined above, NBD means norbornadiene, Ph denotes a phenyl group, acac stands for acetylacetonato, and M is rhodium.

[M(L) $(C_2H_4Cl)$], [M(L) $(C_2H_4)Br$], [M(L) $(C_2H_4)F$], [M(L) $(C_2H_4)I$], [M(L) $(C_2H_4CN)$], [M(L) (CO)Cl], [M(L) (CO)Br], [M(L) (CO)F], [M(L) (CO)I], [M(L) (CO)CN], [M(L) (COD)]Cl, [M(L) (COD)]Br, [M(L) (COD)]F, [M(L) (COD)]I, [M(L) (COD)]$ClO_4$, [M(L) (COD)]$BF_4$, [M(L) (COD)]$PF_6$, [M(L) (COD)CN, [M(L) (COD)$OCOCH_3$, [M(L) (NBD)]Cl, [M(L) (NBD)]Br, [M(L) (NBD)]F, [M(L) (NBD)]I, [M(L) (NBD)]$ClO_4$, [M(L) (NBD)]$BF_4$, [M(L) (NBD)]$PF_6$, [M(L) (NBD)]CN, [M(L) (NBD)]$OCOCH_3$, [M(L) $(CO)_2$]H, [M(L) $(CO)_2(PPh_3)_2$], [M(L) $(CO)_3(PPh_3)$], [M(L) (pyridine)Cl], [M(L) (pyridine)Br] and [M(L) (acac)].

When the transition metal-phosphine complex according to the present invention is used as a catalyst for the asymmetric hydroformylation reaction of, for example, an olefin, an intended product can be obtained in a high optical purity which has been unable to be reached so far. Besides, if one of the optically active phosphine compounds of this invention, which respectively has optical rotation of (+) and (−), is selected, and the transition metal-phosphine complex containing the selected compound as a ligand is used as a catalyst, an intended product having a desired absolute configuration in asymmetric synthesis can be obtained in a high optical purity.

Further, when rhodium is used as a transition metal by way of example, the same result as described above can be obtained even when a mixture obtained by adding an excess amount of the phosphine compound to the rhodium-phosphine complex, or mixing 2–4 equivalent weights, based on rhodium, of the phosphine compound (I) of this invention with a catalyst precursor such as commercially-available [Rh(CO)₂(acac)] is used as a catalyst.

Furthermore, if a rhodium carbonyl cluster such as $Rh_6(CO)_{16}$ or $Rh_4(CO)_{12}$ is used as a catalyst precursor, a useful catalyst is provided. Besides, it may be permissible to react $Rh_n(CO)_n$ with a halogen in advance and combine the resultant product with the phosphine compound.

The transition metal-phosphine complex is generally a mononuclear complex in which one transition metal atom is contained in the complex. However, there may be polynuclear complexes containing 2 or more transition metal atoms therein in some cases.

The hydroformylation embodiment of the invention is one which produces an optically active aldehyde (B) as follows:

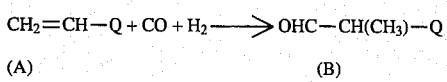

(A)  (B)

wherein Q has the same meaning as defined above.

The catalyst employed in the hydroformylation has formula (2-a) or (2-b) as follows:

wherein L, X and Y have the same meaning as defined above.

The phosphine compound (I), employed as ligand (L), can be synthesized in a high yield in accordance with the reaction scheme described supra.

The phosphine compound thus synthesized is stable in both air and moist air and can be simply purified by column chromatography on silica gel. The values of elemental analysis and spectral data of this compound showed that it surely has a structure of phosphine compound. Its HPLC analysis proved that the compound is optically pure.

The rhodium-phosphine complex useful in the practice of this invention can be synthesized at a good yield from a rhodium complex such as [Rh(CO)₂Cl]₂ and the phosphine compound according to the present invention.

As the rhodium compound used to prepare the hydroformylation catalyst, may be used rhodium metal complexes, mineral acid rhodium salts, organic acid rhodium salts, rhodium oxides and the like. Among a variety of these rhodium compounds, rhodium complexes such as rhodium triacetylacetonate, rhodium dicarbonyl-acetylacetonate, tetrarhodium dodecacarbonyl, hexarhodium hexadecacarbonyl and rhodium cyclooctadieneacetylacetonate, rhodium nitrate, rhodium sulfate, rhodium acetate and rhodium oxides are preferred. Incidentally, the rhodium-phosphine complex is generally a mononuclear complex in which one rhodium atom is contained in the complex. However, there may be polynuclear complexes containing 2 or more rhodium atoms therein in some cases.

Examples of the vinyl compound which is a substrate in the present invention include vinyl chloride, vinyl bromide, vinyl iodide, 1-propene, 1-butene, 1-pentene, 1-hexene, 3,3-dimethyl-1-butene, N-vinylphthalimide, vinyl acetate, vinyl propionate, vinyl valerate, acrylonitrile, acrylic acid, methyl acrylate, ethyl acrylate, butyl acrylate, tert-butyl acrylate, methyl vinyl ether, ethyl vinyl ether, butyl vinyl ether, tert-butyl vinyl ether, 3-butene-2-one, 1-heptene-3-one, 4,4-dimethyl-1-pentene-3-one, N-vinylacetamide, N-vinylbenzamide, methylvinylamine, ethylvinylamine, butylvinylamine, dimethylvinylamine, diethlvinylamine, dibutylvinylamine, styrene, chlorostyrene, bromostyrene, methylstyrene, 4-tert-butyl-styrene, 4-isobutylstyrene, methoxystyrene, ethoxystyrene, vinylnaphthalene, 2-methoxy-6-vinylnaphthalene, 1-chloro-1-propene and 1-bromo-1-propene.

In the process of this invention, it may be permissible to either add the rhodium-phosphine complex, or separately add the rhodium compound and the phosphine compound to the reaction system to form the rhodium-phosphine complex in the system. With respect to the concentration of the catalyst in the reaction system, it is used in an amount corresponding t a range of 0.0001–1,000 milligram atom, preferably 0,001–100 milligram atom in terms of rhodium atom, per liter of a liquid phase.

Although the process of the present invention may be effected without using any reaction solvent, it is generally preferable to conduct a reaction in the presence of a reaction solvent. Any reaction solvent may be used insofar as it does not adversely affect the reaction. However, hydrocarbons are particularly preferred. As specific examples thereof, may be mentioned hexane, heptane, octane, nonane, decane, benzene, toluene, xylene and the like. Besides, preferred examples include ethers such as dipropyl ether, dibutyl ether, tetrahydrofuran and dimethoxyethane, ketones such as diisobutyl ketone and methyl isobutyl ketone, and esters such as butyl butyrate and butyl benzoate.

In the hydroformylation reaction, a process in which water is present in the reaction system is generally preferred for enhancing catalytic activity. In the process of the present invention, water may also be caused to be present in the reaction. No particular limitation is imposed on the amount of water to be added. However, the use of a too small amount of water has little effect. If a too large amount of water is used on the other hand, the effect is not heightened correspondingly. In general, when water is added in an amount 0.001 to 1,000 times by weight of the substrate vinyl compound, the reaction rate may be increased in some cases.

In the process of the present invention, various additives other than water may be added with a view toward improving the activity, positional selectivity and steric selectivity of the catalyst and to improving the stability of the catalyst. When one or more of phosphorus compounds such as phosphine compounds, and besides, triethylphosphine oxide, tributylphosphine oxide, triphenylphosphine oxide, triethylphosphite, tributylphosphite and triphenylphosphite, nitrogen compounds such as fatty acid amines, aromatic amines, pyridine compounds, quinoline compounds, imidazole compounds, diamines, triamines, aminoalcohols and amides, and carboxylic acids such as acetic acid, propionic acid and pivalic acid are present, the activity and the like of the catalyst may be improved in some cases.

With respect to reaction conditions upon effecting the stereoselective hydroformylation process of this invention, the reaction temperature may preferably be within a range of from −20° to 250° C., more preferably from 10° to 150° C. A low reaction temperature is preferred from the viewpoint of the heat stability of aldehydes formed, while a high reaction temperature is desired from the viewpoint of the reaction rate. The reaction may preferably be conducted under a pressure ranging from 5 to 200 kg/cm², more preferably from 20 to 150 kg/cm². In general, the mixing molar ratio of carbon monoxide to hydrogen as raw materials may preferably be within a range of from 10 to 0.1, more preferably from 4 to 0.2. These gases may be diluted with other gases inert to the reaction so far as the mixing ratio of carbon monoxide to hydrogen is maintained to such a range. As the dilute gases, methane, nitrogen, argon, helium, carbon dioxide and the like may be used either singly or in any combination thereof.

The process of the present invention can be conducted by any one of batch, semi-batch and continuous processes. If the reaction is conducted by, for example, the batch process, predetermined amounts of the rhodium-phosphine complex and vinyl compound, and optionally the reaction solvent and additives are charged in an autoclave, in which a mixed gas containing carbon monoxide and hydrogen is introduced to a predetermined pressure. While stirring the contents, they are then heated to a predetermined temperature, whereby the reaction is allowed to progress. In the case of the continuous process, the rhodium-phosphine complex, vinyl compound and additives are dissolved in the solvent. The resulting solution is continuously fed from one side of a pressure reactor by means of a stroke pump, and at the same time, a mixed gas of carbon monoxide and hydrogen is supplied to maintain the reaction pressure constant. The reaction is conducted while stirring the contents under heat, and at the same time, parts of the liquid reaction mixture and mixed gas are continuously drawn out from the other side of the reactor.

The phosphine compound of formula (II) can be prepared by the following reaction scheme:

hydrolyzed or first hydrolyzed and then reduced to obtain 2-diphenylphosphino- 2'-hydroxy-5,5',6,6',7,7',8,8'-octahydro- 1,1'-binaphthyl (8). Compound (8) is reacted with a chlorophosphite derivative (9) in the presence of triethylamine to obtain an optically active phosphine compound of formula (II).

The optically active 1,1'-bi-2-naphthol which can be used as a starting material can easily be prepared in high yield and with high optical purity by reacting optically active 0,0'-dimethyl-N,N'-tetramethyltartaric acid amide prepared from natural or non-natural tartaric acid with one of optical isomers of racemic binaphthol to form a clathrate complex and decomposing the complex.

The transition metal-phosphine complex according to the present invention can be prepared according to known processes, for example, the process described in Nippon Kagakukai (ed.), *JIKKEN KAGAKU KOZA*, 4th Ed., Vol, 18, pp. 254–438.

The transition metal complexes according to the present invention can be synthesized by reacting the phosphine compound (II) with a transition metal compound in an appropriate solvent, such as toluene, benzene, hexane, heptane, isooctane, decane, tetrahydrofuran, diethylether, acetone, methyl ethyl ketone, methylene chloride, and chloroform, and more preferably toluene, benzene, tetrahydrofuran, and methylene chloride.

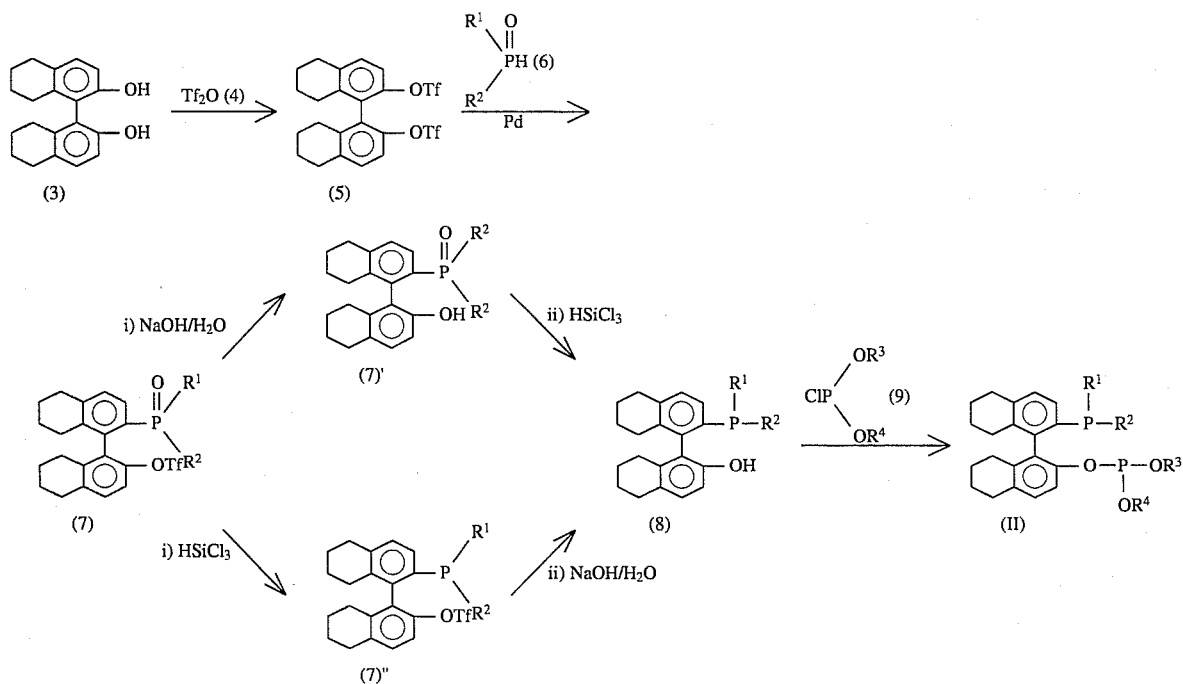

wherein $R^1$, $R^2$, $R^3$ and $R^4$ are as defined above; and Tf represents a trifluoromethanesulfonyl group.

In detail, 2,2'-dihydroxy-5,5',6,6',7,7',8,8'-octahydro-1,1'-binaphthyl (3), which is obtained by hydrogenation of 1,1'-bi-2-naphthol in the presence of a platinum oxide catalyst, is reacted with trifluoromethanesulfonic acid anhydride (4) in accordance with the process described in *Tetrahedron Letters*, Vol. 31, pp. 6321–6324 (1990) to obtain 2,2'-bis(trifluoromethanesulfonyloxy)-5,5',6,6',7,7',8,8-octahydro- 1,1'-binaphthyl (5). Compound (5) is reacted with phosphine oxide (6) in the presence of a palladium catalyst to obtain compound (7). Compound (7) is first reduced by trichlorosilane in the presence of triethylamine and then Specific examples of the transition metal-phosphine complex of the present invention are shown below. In the following formulae, COD represents 1,5-cyclooctadiene; acac represents acetylacetonato; and L represents the phosphine compound of formula (II).

$Ni(L)_2$, $PdCl_2(L)$, ($\pi$-allyl)PdCl(L), [($\pi$-allyl)Pd(L)]ClO$_4$, [($\pi$-allyl)Pd(L)]PF$_6$, [($\pi$-allyl)Pd(L)]BF$_4$, $Pt(L)_2$, Rh(COD)Cl(L), [Rh(COD) (L)]ClO$_4$, [Rh(COD) (L)]PF$_6$, [Rh(COD) (L)]BF$_4$, Rh(acac) (L), Ir(COD)Cl(L), [Ir(COD) (L)]ClO$_4$, [Ir(COD) (L) ]PF$_6$, [Ir(COD) (L)]BF$_4$, [Ru(C$_6$H$_6$)Cl(L) ]Cl, [Ru(p-cymene)Cl(L)]Cl, and (methallyl)Ru(L).

The octahydro binaphthyl skeleton of the phosphine compound (II) may be an optically active compound or a racemate, both of which are included in the scope of the present invention.

When the transition metal-phosphine complex of the present invention is used as a catalyst for, for example, asymmetric hydroformylation of an olefin, a desired product can be obtained in a high asymmetric yield that has never been reached by conventional techniques. By choosing either one of the phosphine isomers, having a plus (+) or (−) optical rotation, and using a transition metal-phosphine complex containing the selected phosphine isomer, a compound having a desired absolute configuration can be obtained by asymmetric synthesis in a high asymmetric yield.

Where rhodium is used as a transition metal, the same reaction results as obtained in using the above-enumerated rhodium-optically active phosphine complex can also be obtained by using the rhodium-phosphine complex in combination with the optically active phosphine compound in excess or a combination of a commercially available rhodium complex, e.g., [Rh(CO)$_2$(acac)], as a catalyst precursor and 2 to 4 equivalents, to rhodium, of the optically active phosphine compound of formula (II).

Further, the same reaction results may also be obtained by using a rhodium-carbonyl cluster, e.g., Rh$_6$(CO)$_{16}$ or Rh$_4$(CO)$_{12}$, as a catalyst precursor. A rhodium-carbonyl cluster Rh$_n$(CO)$_n$ may previously be reacted with a halogen (e.g., chlorine, bromine or iodine) and the reaction product may be used in combination with the optically active phosphine compound of formula (II).

The transition metal-phosphine complex of the present invention is usually a mononuclear complex having a single transition metal atom and, in some cases, may be a polynuclear complex having two or more transition metal atoms.

In a third aspect of the invention, it has now been found that a transition metal complex containing a phosphine compound having an optically active biphenol or binaphthol skeleton as a ligand is markedly superior to known transition metal-optically active phosphine complexes in regio and enantio selectivities in asymmetric hydroformylation and that use of the complex makes it possible to synthesize a variety of optically active aldehydes with ease and particularly a compound which can easily be led to the above compound (III) which is an important intermediate for carbapenem antibiotics.

Specific examples of the phosphine compounds according to the present invention are shown in Tables 1 and 2 below. Abbreviations used in the Tables have the following meaning.

binap: 1,1'-binaphthalene-2,2'-diyl group
bisphenyl: 1,1'-biphenyl 2,2'-diyl group
OcH-binap: 5,5',6,6',7,7',8,8'-octahydro-1,1'-binaphthalene-2,2'-diyl group
Ph: phenyl group
p-MeO: p-methoxyphenyl group
xylyl: 3,5-xylyl group
MeO: methoxy group
p-t-Bu: p-t-butylphenyl group
p-Cl: p-chlorophenyl group
p-Br: p-bromophenyl group
phenanthryl: 10,10'-biphenanthrene-9,9'-diyl

TABLE 1

| No. | $R^7$ | $R^8$ | $R^9$, $R^{10}$ | $R^6$ or $R^{6'}$ | $R^5$ or $R^{5'}$ | $R^{11}$ or $R^{11'}$ |
|---|---|---|---|---|---|---|
| 1 | Ph | Ph | binap | H | H | H |
| 2 | Ph | Ph | binap | Me | H | Me |
| 3 | Ph | Ph | binap | MeO | H | MeO |
| 4 | Ph | Ph | binap | Me | Cl | Me |
| 5 | Ph | Ph | OcH-binap | H | H | H |
| 6 | Ph | Ph | OcH-binap | Me | H | Me |
| 7 | Ph | Ph | biphenyl | Me | Cl | Me |
| 8 | Ph | Ph | biphenyl | MeO | H | MeO |
| 9 | Ph | Ph | Ph, Ph | H | H | H |
| 10 | Ph | Ph | p-Cl, p-Cl | Me | H | Me |
| 11 | p-tol | p-tol | binap | H | H | H |
| 12 | p-tol | p-tol | binap | MeO | H | MeO |
| 13 | p-tol | p-tol | OcH-binap | MeO | Cl | MeO |
| 14 | p-tol | p-tol | biphenyl | H | H | H |
| 15 | p-MeO | p-MeO | binap | MeO | H | MeO |
| 16 | p-MeO | p-MeO | OcH-binap | Me | Cl | Me |
| 17 | xylyl | xylyl | binap | H | H | H |
| 18 | p-t-Bu | p-t-Bu | binap | H | H | H |
| 19 | p-Cl | p-Cl | binap | Me | H | Me |
| 20 | p-Cl | p-Cl | p-t-Bu, p-t-Bu | MeO | Cl | MeO |
| 21 | p-Br | p-Br | binap | Me | H | Me |

TABLE 2

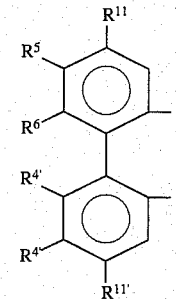

| No. | $R^{11}$ $R^{11'}$ | $R^9$, $R^{10}$ | $R^7$ | $R^8$ |
|---|---|---|---|---|
| 22 | binap | Ph, Ph | Ph | Ph |
| 23 | binap | Ph, Ph | xylyl | xylyl |
| 24 | binap | binap | Ph | Ph |
| 25 | binap | binap | p-Cl | p-Cl |
| 26 | binap | binap | p-t-Bu | p-t-Bu |
| 27 | binap | binap | xylyl | xylyl |
| 28 | binap | binap | p-MeO | p-MeO |
| 29 | binap | biphenyl | Ph | Ph |
| 30 | binap | biphenyl | p-Cl | p-Cl |
| 31 | binap | biphenyl | xylyl | xylyl |
| 32 | binap | OcH-binap | Ph | Ph |
| 33 | binap | OcH-binap | p-MeO | p-MeO |
| 34 | binap | OcH-binap | xylyl | xylyl |
| 35 | binap | phenanthryl | Ph | Ph |
| 36 | OcH-binap | binap | Ph | Ph |
| 37 | OcH-binap | binap | p-Cl | p-Cl |
| 38 | OcH-binap | binap | p-t-Bu | p-t-Bu |
| 39 | OcH-binap | binap | xylyl | xylyl |
| 40 | OcH-binap | biphenyl | Ph | Ph |
| 41 | OcH-binap | biphenyl | p-Cl | p-Cl |
| 42 | OcH-binap | biphenyl | xylyl | xylyl |
| 43 | OcH-binap | OcH-binap | Ph | Ph |
| 44 | OcH-binap | OcH-binap | p-MeO | p-MeO |
| 45 | OcH-binap | OcH-binap | xylyl | xylyl |
| 46 | OcH-binap | phenanthryl | Ph | Ph |
| 47 | OcH-binap | phenanthryl | p-Cl | p-Cl |

The phosphine compound (VII) of the present invention includes optically active compound or non-optically active compound, all of which fall within the scope of the present invention.

The phosphine compound (VII) can be synthesized by, for example, the following reaction route:

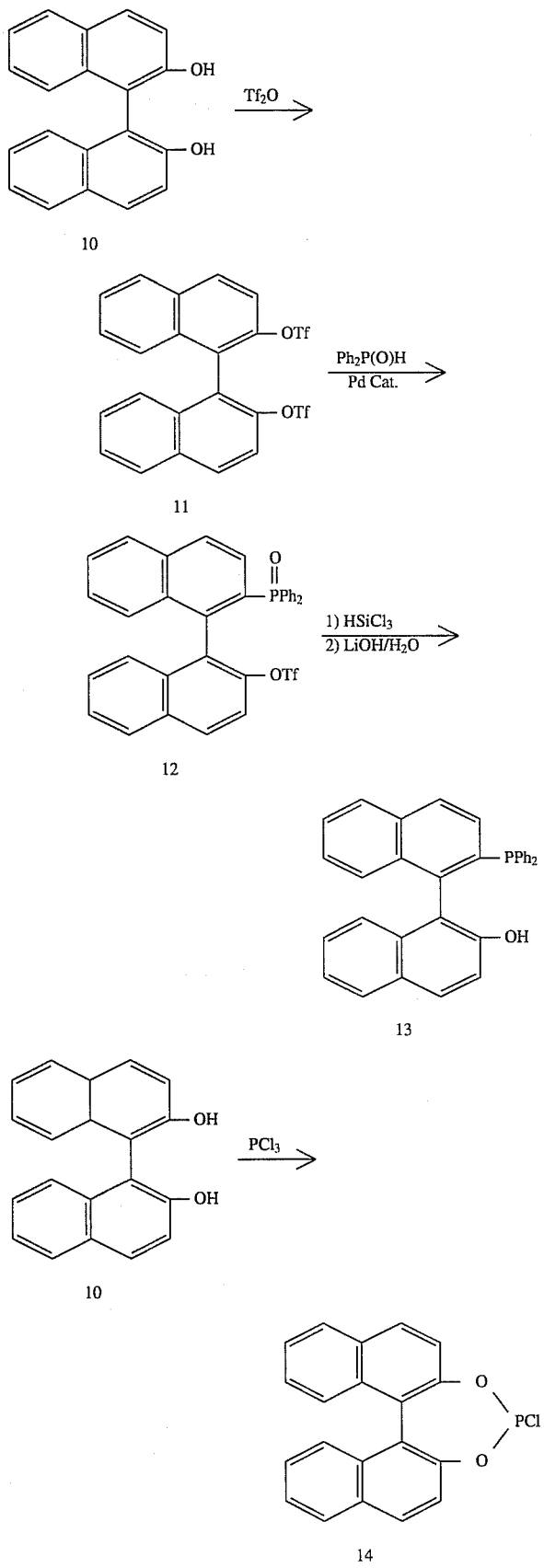

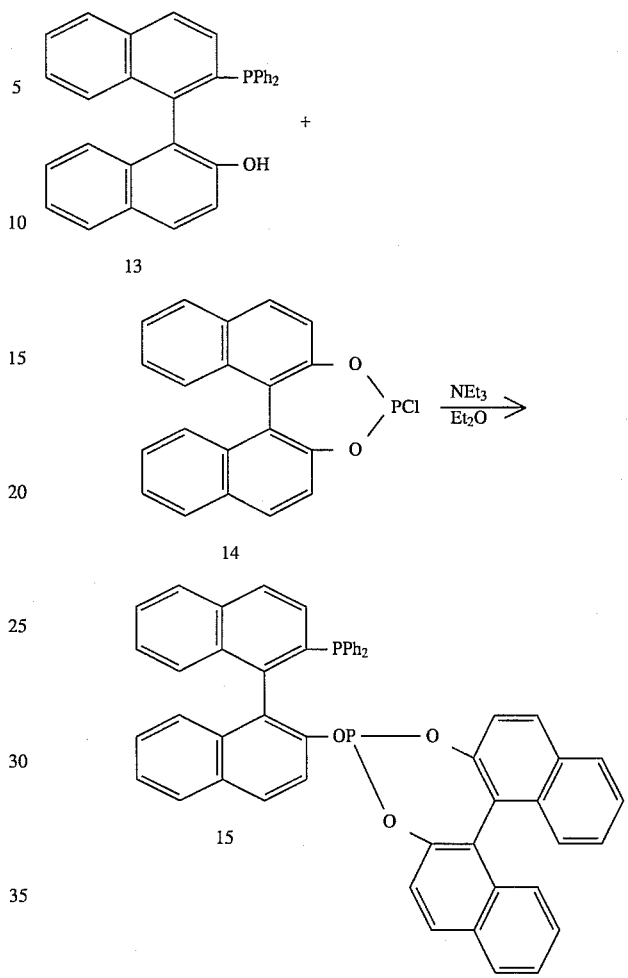

wherein Tf represents a trifluoromethanesulfonyl group; Ph represents a phenyl group; and Et represents an ethyl group.

More specifically, 1,1'-bi-2-naphthol 10 is reacted with trifluoromethanesulfonic acid anhydride to obtain 2,2'-bis-(trifluoromethanesulfonyloxy)- 1,1'-binaphthYl 11 which is then reacted with diphenylphosphine oxide in the presence of a palladium complex catalyst to obtain 2-diphenylphosphinyl-2'-trifluoromethanesulfonyloxy- 1,1'-binaphthyl 12. The compound 12 is reduced by trichlorosilane in the presence of triethylamine and then hydrolyzed to obtain 2-diphenylphosphino- 2'-hydroxy-1,1'-binaphthyl 13. The compound 13 is reacted with a separately synthesized chlorophosphite 14 in the presence of triethylamine to obtain phosphine compound 15 of the present invention.

The phosphine compound (VII) according to the present invention serves as a ligand in the formation of complexes with transition metals. The transition metals capable of forming a complex with the compound (VII) include rhodium, ruthenium, iridium, and platinum. Of these, rhodium is preferred. Of the transition metal complexes according to the present invention, the rhodium complex, for example, can be synthesized by reacting the phosphine compound (VII) with a rhodium compound in an appropriate solvent. The specific examples of the solvent include methylene chloride, hydrocarbons (e.g., toluene, benzene, hexane, heptane, isooctane, decane, etc.), ethers (e.g., diethyl- ether, tetrahydrofuran, etc.), ketones (e.g., acetone, methyl ethyl ketone, etc.), lower alcohols (methanol, ethanol, etc.), and esters (e. g., ethyl acetate). Of these, methylene chloride and toluene are preferred. The rhodium compound as a complex precursor includes $RhCl_3$, $RhBr_3$, $RhI_3$, $Rh_2O_3$, $Rh_2(OAc)_3$ (Ac represents an acetyl group, hereinafter the same), $Rh(O_2C_7H_{15})_2]_2$, $Rh(acac)_3$ (acac represents acetylacetonato, hereinafter the same), $Rh_4(CO)_{12}$, $Rh_6(CO)_{16}$, $[Rh(COD)Cl]_2$ (COD represents 1,5-cyclooctadiene, hereinafter the same), $[Rh(COD)Br]_2$, $[Rh(COD)I]_2$, $[Rh(COD)OAc]_2$, $[Rh(COD)OCOC(CH_3)_3]_2$, $Rh(NBD)Cl]_2$ (NBD represents norbornadiene, hereinafter the same), $[Rh(NBD)Br]_2$, $[Rh(NBD)I]_2$, $[Rh(NBD)OAc]_2$, $[Rh(NBD)OCOC(CH_3)_3]_2$, $Rh(COC)(acac)$, $Rh(NBD(acac)$, $Rh(CO)_2(acac)$, $[Rh(CO)_2Cl]_2$, $[Rh(CO)_2Br]_2$, $[Rh(CO)_2I]_2$, $Rh(CO)_2(Cp)$ (Cp represents 1,3-cyclopentadiene), $Rh(CO)_2(tmCp)$ (tmCp represents 1,2,3,4-tetramethyl-1,3-cyclopentadiene, hereinafter the same), $[Rh(CO)(tmCP)_2]$, $Rh(C_2H_4)_2(acac)$, $[Rh(C_2H_4)_2Cl]_2$, $[Rh(C_2H_4)_2Br]_2$, $[Rh(C_2H_4)_2I]_2$, $[Rh(C_2H_4)_2(tmCp)]$, $RhCl(pph_3)_3$ (Ph represents a phenyl group, hereinafter the same), $RhBr(PPh_3)_3$, $RhI(PPh_3)_3$, $RhH(p(i-Pr)_3)_3$ (i-Pr represents an isopropyl group, hereinafter the same), $RhHCl_2(PPh_3)_2$, $RhHCl_2(AsPh_3)_2$, $RhHCl_2(SbPh_3)_2$, $RhH_2Cl(PPh_3)_2$, $RhH_2Br(PPh_3)_2$, $RhH_2I(PPh_3)_2$, $Rh(OAc)(CO)(PCp_3)_2$, $Rh(OCOPh)(CO)(PCp_3)_2$, $Rh(ClO_4)(CO)(PCp_3)_2$, $Rh(Cl)(CO)(PCp_3)_2$, $Rh(Cl)(CO)(PBu_3)_2$, $Rh(Cl)(CO)(PPh_3)_2$, $Rh(I)(CO)(PCp_3)_2$, $[RhH\{P(O-i-Pr)_3\}_2]_2$, $Rh(C_5H_7O_2)(C_2H_4)$, $[Rh(COD)_2]BF_4$, $[Rh(COD)(CH_3CN)_2]BF_4$, $Rh(COD)(Ph_2P(CH_2)_4PPh_3)]BF_4$, $[Rh(PhCH_3)(Ph_2P(CH_2)_5PPh_3)]BF_4$, $Rh(PhCH_3)\{PPh_2(o-CH_3OC_6H_4)_2\}_2]BF_4$, $[Rh(COD)(PPh_3)_2]PF_6$, $Rh(COD)(AsPh_3)_2]ClO_4$, $[Rh(NBD)(PPh_3)_2]ClO_4$, $[RhH_2(PPh_3)_2(AcCH_3)](C_2H_5OH)]ClO_4$, $[RhH_2(PPh_3)_2(CH_3CN)_2]ClO_4$, $[RhH_2(PPh_3)_2(C_2H_5OH)]ClO_4$, $[RhCl_2(\eta-C_5H_{10}(CH_3)_4)]_2$, $Rh(Cp)(PPh_3)_2$, $[Rh(t-mCp)(CH_3CN)_3](PF_6)_2$, $Rh_2Cl_2(\eta-C_3H_5)_4$, and $Rh(\eta-C_3H_5)_3$.

The rhodium-phosphine complexes usually have one rhodium atom in the molecule thereof (mononuclear complexes) and in some cases have two or more rhodium atoms (polynuclear complexes).

Ruthenium complexes, iridium complexes and platinum complexes containing the phosphine compound (VII) as a ligand can also be prepared in the same manner as described above.

The transition metal-phosphine complexes of the present invention are useful as a catalyst for asymmetric hydroformylation to produce optically active aldehydes.

Optically active aldehydes can also be prepared by hydroformylation of olefins in the presence of the phosphine compound (VII). That is, hydroformylation of an olefin proceeds in the presence of a transition metal compound and the phosphine compound (VII) separately added and mixed in a reaction solvent to form a transition metal-phosphine complex in situ thereby to produce an optically active aldehyde similarly to the case of using a previously prepared transition metal-phosphine complex. This will be proved from the following fact.

Where a transition metal compound, e.g., $Rh(CO)_2(acac)$ and the phosphine compound (hereinafter abbreviated as "phos") are reacted at an equivalent ratio in a solvent, e.g., methylene chloride, ligand exchange takes place between two carbonyl groups and phos to form an Rh(acac)(phos) type complex. On $^{31}P$-NMR analysis of the isolated complex, there are revealed two signals. Where one equivalent of $Rh(CO)_2(acac)$ and 2.5 equivalents of phos are similarly reacted in a solvent, the $^{31}P$-NMR spectrum shows two signals assigned to phos per se in addition to those to the complex. On the other hand, the system containing one equivalent of $Rh(CO)_2(acac)$ and 2.5 equivalents of phos under hydroformylation reaction conditions (before addition of carbon monoxide and hydrogen) similarly shows signals both of the complex and phos. From these results, it is seen that the reaction necessarily proceeds via formation of Rh(acac)(phos).

Illustrative examples of olefins which can be used as a reaction substrate in the present invention include vinyl chloride, vinyl bromide, vinyl iodide, 1-propene, 1-butene, 1-pentene, 1-hexene, 3,3-dimethyl-l-butene, N-vinylphthalimide, vinyl acetate, vinyl propionate, vinyl valerate, acrylonitrile, acrylic acid, methyl acrylate, ethyl acrylate, butyl acrylate, t-butyl acrylate, methyl vinyl ether, ethyl vinyl ether, butyl vinyl ether, t-butyl vinyl ether, 3-buten- 2-one, 1-buten-3-one, 1-hepten-3-one, 4,4-dimethyl-l-penten-3-one, 1-phenyl-2-propen-l-one, N-vinylacetamide, N-vinylbenzamide, methylvinylamine, ethylvinylamine, butylvinylamine, dimethylvinylamine, diethylvinylamine, dibutylvinylamine, styrene, chlorostyrene, bromostyrene, methylstyrene, 4-t-butylstyrene, 4-isobutylstyrene, methoxystyrene, ethoxystyrene, vinylnaphthalene, 2-methoxy-6-vinylnaphthalene, 1-chloro-1-propene, 1-bromo-1-propene, 2-butene, 2-pentene, 2-hexene, 2-heptene, 1-propenyl acetate, 1propenyl cyanide, crotonic acid, methyl crotonate, butyl crotonate, methyl 1-propenyl ether, 3-penten-2-one, 2-octen-4-one, N-2-pentenylacetamide, methyl 2-propenylamine, butyl 2-propenylamine, dimethyl 2-propenylamine, dibutyl 2-propenylamine, 4-(2-propenyl)chlorobenzene, 4-(2propenyl)toluene, 4-(2-propenyl)butylbenzene, (1'R,3S, 4R)-3-( 1'-(Pro-1-)oxy)ethyl-4-vinylazetizin-2-one, indene, and 1,2-dihydronaphthalene.

"Pro-1" as used above corresponds to $R_1$ in formula (X), including a hydrogen atom and a hydroxyl-protecting group. Examples of the hydroxyl-protecting group include substituted silyl groups, e.g., trimethylsilyl, triethylsilyl, isopropyldimethylsilyl, t-butyldimethylsilyl, (triphenylmethyl)dimethylsilyl, t-butyldiphenylsilyl, methyldiisopropylsilyl, methyl-di-t-butylsilyl, tribenzylsilyl, tri(p-tolyl)silyl, triisopropylsilyl, and triphenylsilyl; acyl groups, e.g., formyl, benzoylformyl, acetyl, chloroacetyl, dichloroacetyl, trichloroacetyl, trifluoroacetyl, methoxyacetyl, phenoxyacetyl, p-chlorophenoxyacetyl, benzoyl, benzyloxycarbonyl, and ethoxycarbonyl; and aralkyl groups, e.g., benzyl, benzhydryl, and triphenylmethyl. $R_1$ is preferably a hydrogen atom, a trimethylsilyl group, a t-butyldimethylsilyl group, a benzyloxycarbonyl group, an ethoxycarbonyl group, an acetyl group, a benzyl group, a benzhydryl group, and a triphenylmethyl group.

The hydroformylation can be carried out by adding to a reaction system the phosphine compound (VII) and a compound of a transition metal selected from rhodium, ruthenium, iridium, and platinum separately or the transition metal-phosphine complex previously formed from a compound of a transition metal selected from rhodium, ruthenium, iridium, and platinum and the phosphine compound (VII). The complex catalyst or catalyst system is added in an amount of preferably from 0.0001 to 1000 mg, and more preferably from 0,001 to 100 mg, per liter of the liquid phase in terms of the transition metal atom. The phosphine compound (VII) is preferably used in an amount 1 to 5 times, and more preferably 2 to 4 times, the mole number of the metal atom.

While the hydroformylation may be effected in the absence of a reaction solvent, use of a reaction solvent is generally recommended. The reaction solvent to be used is not particularly limited as long as it does not adversely affect the reaction. Hydrocarbon solvents, e.g., hexane, heptane, octane, isooctane, nonane, decane, cyclohexane, cyclopentane, benzene, toluene, xylene, and mesitylene, are especially preferred. In addition, ethers, e.g., diisopropyl ether, dibutyl ether, tetrahydrofuran, dimethoxyethane, and diethylene glycol dimethyl ether; ketones, e.g., diisobutyl ketone, methyl isobutyl ketone, acetone, and methyl ethyl ketone; esters, e.g., ethyl acetate, butyl butyrate, and butyl benzoate; and alcohols, e.g., methanol, ethanol, butanol, and t-butanol; are also usable. These solvents may be used either individually or in combination thereof.

It is generally preferred to conduct hydroformylation in the presence of water in order to enhance the catalytic activity. In the present invention, too, water may be present in the reaction system. While the amount of water to be added is not limited, an extremely small amount of water produces no essential effect, and an extremely large amount of water adds not further improvement. An increase of reaction rate is often obtained by addition of water in an amount 0,001 to 1000 times the weight of the olefin substrate.

For the purpose of improving catalytic activity, regio and enantio selectivities, various additives other than water may be added to the reaction system. For example, presence of phosphorus compounds, e.g., triethylphosphine oxide, triphenylphosphine oxide, tributylphosphine oxide, triethyl phosphite, tributyl phosphite, and triphenyl phosphite; or carboxylic acids, e.g., acetic acid, propionic acid and pivalic acid, in the reaction system gives rise to no interference with the reaction.

The hydroformylation temperature usually ranges from −20° to 250° C., and preferably from 10° to 150° C. Within this range, low temperatures are preferred from the standpoint of thermal stability of the resulting aldehyde, while high temperatures are preferred from the viewpoint of reaction rate. The reaction pressure usually ranges from 5 to 200 kg/cm$^2$, and preferably from 20 to 150 kg/cm$^2$. Carbon monoxide and hydrogen are usually fed to the reaction system at a molar ratio of from 0.1 to 10, and preferably from 0.2 to 4. As far as the carbon monoxide to hydrogen molar ratio falls within this range, the mixed gas may be diluted with an inert gas, such as methane, nitrogen, argon, helium, and carbon dioxide, either individually or in combination thereof.

According to the present invention, a 4-[(R)-1'-formylethyl]acetidin-2-one derivative represented by formula

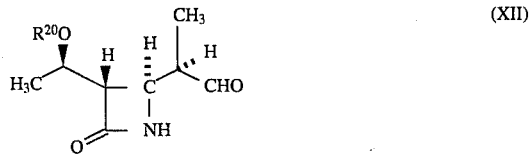

wherein R$^{20}$ is as defined above, can be prepared in excellent optical purity with high regioselectivity by subjecting a compound represented by formula (XIII):

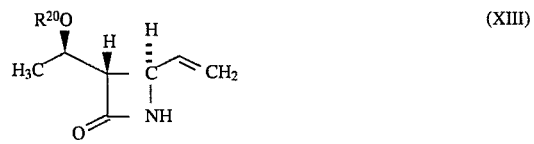

wherein R$^{20}$ is as defined above, to the above-mentioned hydroformylation process. The starting compound of formula (XIII) is obtained, for example, by the process described in *Liebig Ann. Chem.*, pp. 539–560 (1974) as follows. A 4-acetoxyazetidin-2-one derivative represented by formula (XIV):

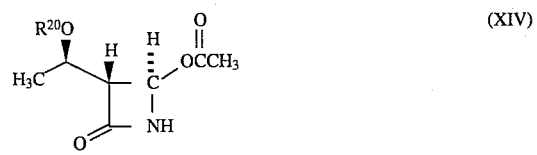

wherein R$^{20}$ is as defined above, is reacted with a sodium, potassium or lithium salt of benzenesulfinic acid or p-toluenesulfinic acid in a soluble solvent, e.g., acetone-water, methanol or water-methanol, to obtain a compound represented by formula (XV):

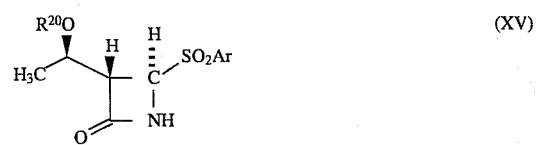

wherein R$^{2°}$ is as defined above; and Ar represents a phenyl group which may be substituted with a halogen atom, a lower alkyl group, etc.

The compound (XV) is then reacted with an organic vinyl compound as a vinylating agent, such as vinylmagnesium chloride, vinylmagnesium bromide, vinylmagnesium iodide, divinylmagnesium, vinyllithium, vinylzinc chloride or divinylzinc, in accordance with the procedure described in *J. Chem. Soc. Chem. Commn.*, pp. 736–737 (1980) to obtain the compound (VI).

The compound (XII) can be obtained by hydroformylation of the thus prepared compound (XIII) in the presence of the transition metal-phosphine complex of the present invention or both the phosphine compound (VII) and a transition metal compound.

It is essentially required for obtaining the compound (XII) in which the 1'-formyl group has an R-configuration, i.e., a β-compound that the skeleton moiety of the phosphine compound (VII) should have an R-configuration and that the phosphinite moiety as a counterpart, when derived from an axially dissymmetric diol, should have an S-configuration.

The formyl group of the compound (XII) can easily be converted to a carboxyl group by an ordinary oxidation reaction, for example, Jones oxidation to provide the compound of formula (XIII), an important intermediate for carbapenem antibiotics.

According to the present invention, optically active aldehydes useful as pharmaceuticals, agricultural chemicals, perfumes, etc. or intermediates therefor can be synthesized in a high optical purity.

Having generally described this invention, a further understanding can be obtained by reference to certain specific examples which are provided herein for purposes of illustration only and are not intended to be limiting unless otherwise specified.

Measuring instruments used in Examples are as follows.
Nuclear Magnetic Resonance Spectrum (NMR):
  Model EX-270 manufactured by JEOL Ltd.
  Model AM-400 manufactured by Bruker, Inc.
Internal Standard:
  $^1$H-NMR: tetramethylsilane
External Standard:
  $^{31}$P-NMR: 85% phosphoric acid
Optical Purity:
  GC-15A Gas Chromatograph manufactured by Shimadzu Corporation
  Column: Chiral capillary column, CHROMPACK β-236M Chemical Purity:
  Hitachi 263-30 Gas Chromatograph manufactured by Hitachi, Ltd.
Optical Rotation:
  Model DIP-360 (manufactured by JASCO Inc.)
  Model DIP-4 360 (manufactured by Japan Spectroscopic Co.; Ltd. )
  The abbreviations of the makers of reagents used in the examples have the following meanings:
  Wako: Wako Pure Chemical Industries, Ltd.
  Tokyo: Tokyo Kasei Kogyo Co., Ltd.
  Ald: Aldrich Japan Ink Co., Inc.
  NACALAI: NACALAI TESQUE INC.

EXAMPLE 1

Synthesis of (R)-2-diphenylphosphino-1,1'-binaphthalene- 2'-yloxy((S)-1,1'-binaphthalene-2,2'-diyldioxy)phosphine:

(1) Synthesis of (R)-2,2'-bis(trifluoromethanesulfonyloxy)- 1,1'-binaphthyl:

In a 100-ml flask, 5 g (17.4 mmol) of (R)-1,1'-bi-2-naphthol (product of Mitsubishi Gas Chemical Company, Inc.), 5.58 g (52.2 mmol) of 2,6-lutidine (Tokyo) and 0.955 g (7.83 mmol) of 4-dimethylaminopyridine (Wako) were dissolved in 26 ml of methylene chloride, to which 14.7 g (52.2 mmol) of trifluoromethanesulfonic anhydride (Wako) was added at 0° C. to react them for 23 hours at room temperature with stirring. After completion of the reaction, the solvent was distilled off, and the residue was then purified by column chromatography on silica gel making use of methylene chloride as a developing solvent to obtain 9.56 g (yield: 100%) of (R)-2,2'-bis(trifluoromethanesulfonyloxy)-1,1'-binaphthyl.

(2) Synthesis of (R)-2-diphenylphosphinyl-2'-trifluoromethanesulfonyloxy- 1,1'-binaphthyl:

In a 100-ml 4-necked flask, 2.74 g (4.98 mmol) of (R)-2,2'-bis(trifluoromethanesulfonyloxy)-1,1'-binaphthyl prepared in the step (1) and 1.99 g (9.82 mmol) of diphenylphosphine oxide (Tokyo) were dissolved in 20 ml of dimethylsulfoxide in an argon stream, to which 110 mg (0,491 mmol) of palladium acetate, 203 mg (0,491 mmol) of 1,3-bis(diphenylphosphino)propane, 5.1 ml of ethyldiisopropylamine (Ald) and 33 mg (0,491 mmol) of sodium formate (NACALAI) were combined to stir them for 20 minutes at room temperature. Thereafter, the resultant solution was stirred for 19 hours at 90° C. and then cooled back to room temperature. The solution was added with 250 ml of ether and 150 ml of water, and the mixture was stirred to separate an organic layer andan aqueous layer. After the separation, the organic layer was washed four times with 125 ml of water, twice with 125 ml of 5% diluted hydrochloric acid, twice with 50 ml of water, once with 125 ml of a saturated aqueous solution of sodium hydrogencarbonate and lastly with 125 ml of a brine. The thus-washed organic layer was dried on anhydrous magnesium sulfate, and the solvent was distilled off. The residue was then purified by column chromatography on silica gel making use o# a 3:1 (solvent ratio, the same shall apply hereinafter) mixture of toluene and acetonitrile as a developing solvent, thereby obtaining 2.51 g (yield: 83%) of the title compound.

(3) Synthesis of (R)-2-diphenylphosphino-2'-hydroxy-1,1'-binaphthyl:

In a 50-ml 3-necked flask, 400 mg (0,664 mmol) of (R)-2-diphenylphosphinyl- 2'-trifluoromethanesulfonyloxy-1,1'-binaphthyl prepared in the step (2) was dissolved in 22 ml of xylene, to which 1.21 g (12 mmol) of triethylamine (Wako) and 1.62 g (12 mmol) of trichlorsilane (Ald) were added. The resulting mixture was stirred for 17 hours at 120° C. After the reaction mixture was cooled back to room temperature, 4.4 ml of 35% aqueous sodium hydroxide was carefully added thereto, and the mixture was stirred further for 2 hours, followed by separation of an organic layer and an aqueous layer. After the separation, the organic layer was washed twice with 30 ml of a brine and then dried on anhydrous magnesium sulfate, and the solvent was distilled off under reduced pressure, thereby obtaining a crude product. The crude product was dissolved in 7 ml of tetrahydrofuran, to which a solution of 335 mg (7.98 mmol) of lithium hydroxide (Wako) in 2.4 ml of water was added. The resulting mixture was stirred for 15 hours at room temperature, to which 50 ml of ether and 15 ml of 5% diluted hydrochloric acid were added to separate an organic layer and an aqueous layer. After the organic layer was washed twice with water, it was dried on anhydrous magnesium sulfate, and the solvent was distilled off. The residue was then purified by column chromatography on silica gel making use of a 5:1 mixture of hexane and ethyl acetate as a developing solvent, thereby obtaining 153 mg (yield: 51%) of the title compound. (4) Synthesis of (S)-1,1'-binaphthalene-2,2'-diyldioxychlorophosphine:

A 50-ml flask equipped with a reflux condenser was charged with 4.94 g (17.3 mmol) of (S)-1,1'-bi-2-naphthol (product of Mitsubishi Gas Chemical Company, Inc.) and 113 g (0.83 mol) of phosphorus trichloride (Wako) in an argon stream to reflux the mixture for 4 hours. Thereafter, the reaction mixture was cooled back to room temperature, and unreacted phosphorus trichloride was distilled off under reduced pressure, thereby obtaining 5.56 g (yield: 92%) of the title compound as white crystals. (5) Synthesis of (R)-2-diphenylphosphino-1,1'-binaphthalene- 2'-yloxy((S)-1,1'-binaphthalene-2,2'-diyldioxy)phosphine:

In a 100-ml flask, 430 mg (0,946 mmol) of (R)-2-diphenylphosphino- 2'-hydroxy-1,1'-binaphthyl prepared in the step (3) and 662 mg (1.89 mmol) of (S)-1,1'-binaphthalene- 2,2'-diyldioxychlorophosphine prepared in the step (4) were dissolved in 30 ml of ether, to which 191 mg (1.89 mmol) of triethylamine was added at 0° C. After the mixture was stirred for 15 hours at room temperature, 20 ml of water was added to stop the reaction. After separating an organic layer and an aqueous layer, the organic layer was dried on anhydrous magnesium sulfate, and the solvent was distilled off, thereby obtaining a crude product. The crude product was purified by column chromatopgraphy on silica gel making use of a 1:1 mixture of hexane and dichloromethane as a developing solvent, thereby obtaining 712 mg (yield: 98%) of the title compound, (R)-2-diphenylphosphino-1,1'-binaphthalene-2'-yloxy-((S)-1,1'-binaphthalene- 2,2'-diyldioxy)phosphine [hereinafter called "(R,S)-BINAPHOS"] as white crystals. $^{31}$P-NMR (CDCl$_3$) δ:- 14.6(d,J=29.0Hz), 144.7(d,J=29.0Hz).

EXAMPLE 2

Synthesis of (R)-2-(diphenylphosphino)-1,1'-binaphthalene- 2'-yloxy((R)-1,1'-binaphthalene-2,2'-diyldioxy)phosphine:

A 100-ml flask was charged with 30 ml of ether, to which 209 mg (0.46 mmol) of (R)-2-diphenylphosphino-2'-hydroxy-1,1'-binaphthyl prepared in the step (3) of Example 1 and 322 mg (0.92 mmol) of (R)-1,1'-binaphthalene-2,2'-diyldioxychlorophosphine were added to dissolve them in ether. To the solution, 191 mg (1.89 mmol) of triethylamine triethylamine was added at 0° C. Thereafter, the same procedure as in Example 1 was followed to obtain 353 mg (yield: 96.3%) of the title compound, (R)-2-(diphenylphosphino)- 1,1'-binaphthalene-2'-yloxy((R)-1,1'-binaphthalene-2,2'-diyldioxy)phosphine [hereinafter called "(R,R)-BINAPHOS"] in the form of a pale yellow solid. $^{31}$P-NMR (CDCl$_3$) δ: −18.0(d,J=9.2Hz), 140.5(d,J=9.2Hz).

EXAMPLE 3

Synthesis of (R)-2-(diphenylphosphino)-1,1'-binaphthalene- 2'-yloxy(diphenoxy)phosphine:

The same procedure as in the step (5) of Example 1 was followed except that chlorodiphenoxyphophine was used in place of (S)-1,1'-binaphthalene-2,2'-diyldioxychlorophosphine, thereby obtaining the title compound, (R)-2-(diphenylphosphino)- 1,1'-binaphthalene-2,-yloxy(diphenoxy)phosphine [hereinafter called "(R)-Ph-BINAPHOS"] in the form of a pale yellow solid at a yield of 77%. $^{31}$P-NMR (CDCl$_3$) δ: −10.6(d,J=13.7Hz), 129.2(d,J=13.7Hz).

EXAMPLE 4

Synthesis of (R)-2-(di-(3,5-xylyl)phosphino)-1,1'-binaphthalene- 2'-yloxy((S)-1,1'-binaphthalene-2,2'-diyldioxy)phosphine:

The same procedure as in the step (5) of Example 1 was followed except that (R)-2-(di-(3,5-xylyl)phosphino)2,-hydroxy- 1,1'-binaphthyl was used in place of (R)-2-diphenylphosphino- 2'-hydroxy-1,1'-binaphthyl, thereby obtaining the title compound, (R)-2-(di-(3,5-xylyl)phosphino)-1,1'-binaphthalene-2'-yloxy((S)-1,1'-binaphthalene-2,2'-diyldioxy) phosphine [hereinafter called "(R, S) -Me-BINAPHOS"] in the form of a pale yellow solid at a yield of 98%.

$^{31}$P-NMR (CDCl$_3$) δ: −12.4(d,J=32.0Hz), 145.5 (d)

EXAMPLE 5

Synthesis of Rh((R)-Ph-BINAPHOS) (acac):

A 20-ml Schlenk's tube was charged 7 mg (0,025 mmol) of (R)-Ph-BINAPHOS prepared in Example 3 and 6.5 mg (0,025 ml) of Rh(CO)$_2$(acac) (acac means acetylacetonato, the same shall apply hereinafter) (product of Ald) to dissolve them in 5 ml of methylene chloride. After the reaction mixture was stirred for 5 minutes at room temperature, the solvent was distilled off under reduced pressure to obtain 22 mg (yield: 100%) of Rh( (R) -Ph-BINAPHOS)(acac) as a yellow solid.

$^{31}$P-NMR (CDCl$_3$) δ: 51.1(dd,J$_{p-p}$=82.4Hz,J$_{Rh-p}$=174.0Hz), 138.8 (dd, J$_{Rh-p}$=328.1Hz).

EXAMPLE 6

Synthesis of Rh((R,S)-BINAPHOS)(acac):

The same procedure as in Example 5 was followed except that (R,S)-BINAPHOS prepared in Example 1 was used in place of (R)-Ph-BINAPHOS used in Example 5, thereby obtaining 63 mg (yield: 99%) of Rh((R,S)-BINAPHOS)(acac).

$^{31}$P-NMR (CDCl$_3$) δ: 48.3(dd,J$_{p-p}$=83.9Hz,J$_{Rh-p}$=174.0Hz) , 161.8 (dd,J$_{Rh-p}$=331.1 Hz).

EXAMPLE 7

Synthesis of Rh((R,R)-BINAPHOS) (acac):

The same procedure as in Example 5 was followed except that (R,R)-BINAPHOS prepared in Example 2 was used in place of (R)-Ph-BINAPHOS used in Example 5, thereby obtaining 63 mg (yield: 99%) of Rh((R,R)-BINAPHOS)(acac).

$^{31}$P-NMR (CDCl$_3$) δ: 51.9(dd,J$_{p-p}$=80.8 Hz,J$_{Rh-p}$=178.4 Hz), 152.5 (dd,J$_{Rh-p}$=335.1 Hz).

EXAMPLE 8

Synthesis of Rh((R,S)-Me-BINAPHOS) (acac):

The same procedure as in Example 5 was followed except that (R,S)-Me-BINAPHOS prepared in Example 4 was used in place of (R)-Ph-BINAPHOS used in Example 5, thereby obtaining 37 mg (yield: 99%) of Rh((R,S)-MeBINAPHOS)(acac).

$^{31}$P-NMR (CDCl$_3$) δ: 48.8(dd,J$_{p-p}$=82.4 Hz,J$_{Rh-p}$=172.4 Hz), 160.9 (dd, J$_{Rh-p}$=332.6 Hz).

Reference Example 1

Asymmetric hydroformylation reaction of vinyl acetate:

A 50-ml autoclave was charged with 1,301 g (15.13 mmol) of vinyl acetate (Wako), 9.8 mg (0.0378 mmol) of Rh(CO)$_2$(acac) as a catalyst precursor, 58 mg (0.0755 mmol) of (R,S)-BINAPHOS as an optically active phosphine and 14 ml of benzene. The contents were stirred at 60° C. for 112 hours under a hydrogen pressure of 50 atm and a carbon monoxide pressure of 50 atm. The determination of conversion of vinyl acetate and the analysis of the reaction products were conducted by gas chromatography (10% SE-30 on Chromosorb W 80–100 mesh packed in a 5 mm×2 m glass column), and the optical purities of the products were determined by optically active gas chromatography (Astec Chiraldex B-PH). As a result, it was found that compounds produced by this reaction were a mixture of 90% of 2-acetoxypropanal and 10% of 3-acetoxypropanal, and the conversion was 98%. 2-Acetoxypropanal was then distilled to determine its optical purity. As a result, it was found to be 90% ee. This compound was then caused to undergo Jones oxidation to prepare 2-acetoxypropionic acid. Its optical rotation was measured. As a result, it was confirmed that the compound is (S)-(−)-2-acetoxypropionic acid.

Reference Example 2

Asymmetric hydroformylation reaction of vinyl acetate:

The same procedure as in Reference Example 1 was followed except that Rh((R,R)-BINAPHOS) (acac) was used as a catalyst, and the reaction was conducted for 37 hours at 50° C., thereby obtaining a mixture of 92% of 2-acetoxypropanal and 8% of 3-acetoxypropanal. The conversion was 46%. The optical purity of 2-acetoxypropanal after distillation was determined in the same manner as in Reference Example 1, and was found to be 73% ee. This compound was then caused to undergo Jones oxidation to prepare 2-acetoxypropionic acid. Its optical rotation was measured. As a result, it was confirmed that the compound is (S)-(−)-2-acetoxypropionic acid.

Reference Example 3

Asymmetric hydroformylation reaction of styrene:

A 50-ml autoclave was charged with 3.06 g (29.4 mmol) of styrene (NACALAI), 3.7 mg (0.0143 mmol) of Rh(CO)$_2$(acac), 44 mg (0.0573 mmol) of (S,R)-BINAPHOS and 1 ml of benzene-$d_6$. The contents were stirred at 60° C. for 43 hours under a hydrogen pressure of 50 atm and a carbon monoxide pressure of 50 atm. After completion of the reaction, the reaction mixture was cooled back to room temperature, and the gases under pressure were removed. Thereafter, the reaction mixture was directly analyzed by $^1$H-NMR. As a result, it was found that the conversion of styrene was at least 99%, and a mixture of 88% of 2-phenylpropanal and 12% of 3-phenylpropanal as reaction products was obtained in an amount of 1,273 g. No other products were observed. 2-Phenylpropionic acid was derived in the same manner as in Reference Example 1 to determine its optical purity. As a result, it was confirmed that the compound is (S)-(+)-2-phenylpropionic acid having an optical purity of 94% ee.

EXAMPLE 9

Synthesis of (R)-2-Diphenylphosphino- 5,5',6,6',7,7',8,8'-octahydro-1,1'-binaphthalen-2-yloxy-((S)- 1,1'-binaphthalene-2,2'-diyldioxy)phosphine (1) Synthesis of 5,5',6,6',7,7',8,8'-Octahydro-1,1'-bi-2-naphthol:

In a 200 ml autoclave were charged 3.00 g (10.5 mmol) (R)-2,2'-dihydroxy-1,1'-binaphthyl, 360 mg of platinum dioxide, and 75 ml of acetic acid, and the mixture was stirred at 5° C. for 18 hours under a hydrogen pressure of 3 atm and then at 18° C. for 7 days under a hydrogen pressure of 10 atm. Ethyl acetate was added to the reaction mixture, and the mixture was filtered through Celite. Water was added to the filtrate, followed by liquid-liquid separation. The separated organic layer was washed twice with a saturated sodium hydrogencarbonate aqueous solution, followed by liquid-liquid separation. The organic layer was dried over magnesium sulfate, and the solvent was removed by distillation under reduced pressure to obtain 3.03 g (percent yield: 98%) of the titled binaphthol. Optical purity: ≧99% ee. (2) Synthesis of (R)-2,2'-Bis(trifluoromethanesulfonyloxy)-5,5',6,6',7,7',8,8'-octahydro-1,1'-binaphthyl:

In a 50 ml four-necked flask was put a solution of 7.36 g (25 mmol) of (R)-5,5',6,6',7,7',8,8'-octahydro-1,1'-2-naphthol and 6 ml (74 mmol) of pyridine in 50 ml of methylene chloride, and 15.5 g (55 mmol) of trifluoromethanesulfonic acid anhydride was added to the solution at 0° C., followed by stirring at room temperature for 23 hours to complete the reaction. After completion of the reaction, the solvent was removed by distillation, and the residue was purified by silica gel column chromatography using a 10:1 (by volume; hereinafter the same) mixture of hexane and ethyl acetate as a developing solvent to obtain 12.88 g (percent yield: 92%) of (R)-2,2'-bis(trifluoromethanesulfonyloxy)-5,5',6,6',7,7',8,8'-octahydro-1,1'-binaphthyl.

(3) Synthesis of (R)-2-Diphenylphosphinyl-2'-trifluoromethanesulfonyloxy- 5,5',6,6',7,7',8,8'-octahydro-1',1-binaphthyl:

In a 50 ml flask was charged a solution of 2.68 g (4.80 mmol) of (R)-2,2'-bis(trifluoromethanesulfonyloxy)- 5,5',6,6',7,7',8,8'-octahydro-1,1'-binaphthyl obtained in (2) above and 1.99 g (9.04 mmol) of diphenylphosphine oxide in 20 ml of dimethylsulfoxide in an argon stream. To the solution were added 108 mg (0.480 mmol) of palladium acetate, 205 mg (0.480 mmol) of 1,4-bis(diphenylphosphino)butane, 5.1 ml of ethyldiisopropylamine, and 33 mg (0,491 mmol) of sodium formate, and the mixture was stirred at room temperature for 20 minutes and then at 90° C. for 19 hours. After cooling to room temperature, 250 ml of ethyl ether and 150 ml of water were added to the reaction mixture, followed by stirring and liquid-liquid separation.

The organic layer thus separated was washed succcessively with four 125 ml portions of water, two 125 ml portions of 5% dilute hydrochloric acid, two 50 ml portions of water, a 125 ml portion of a saturated sodium hydrogencarbonate aqueous solution, and a 125 ml portion of a saturated sodium chloride aqueous solution and dried over anhydrous magnesium sulfate. The solvent was distilled off, and the residue was purified by silica gel column chromatography using a 2:1 to 1:1 mixture of hexane and ethyl acetate as a developing solvent to obtain 2.76 g (percent yield: 94%) of the titled compound.

(4) Synthesis of (R)-2-Diphenylphosphino-2'-hydroxy-5,5',6,6',7,7',8,8'-octahydro-1,1'-binaphthyl:

In a mixed solvent of 3 ml of 1,4-dioxane and 2 ml of methanol was dissolved 405.4 mg (0.664 mmol) of (R)-2-diphenylphosphinyl- 2'-trifluoromethanesulfonyloxy- 5,5',6,6',7,7',8,8'-octahydro-1,1'-binaphthyl, and 3 ml of a 3N sodium hydroxide aqueous solution was added thereto, followed by stirring at room temperature for 15 hours. The reaction mixture was made acidic with concentrated hydrochloric acid and poured into 50 ml of water. The thus precipitated solid was collected by filtration to obtain a crude product. The crude product was dissolved in 22 ml of xylene in a 50 ml four-necked flask, and 1.21 g (12 mmol) of triethylamine and 1.62 g (12 mmol) of trichlorosilane were added to the solution, followed by stirring at 120° C. for 17 hours. After cooling to room temperature, 4.4 ml of a 35% sodium hydroxide aqueous solution was carefully added to the reaction mixture. The mixture was stirred for 2 hours, followed by liquid-liquid separation.

The separated organic layer was washed with two 30 mE portions of a saturated sodium chloride aqueous solution, dried over anhydrous magnesium sulfate, and distilled to remove the solvent. The residue was purified by silica gel column chromatography using a 5:1 mixture of hexane and ethyl acetate as a developing solvent to obtain 245.8 mg (percent yield: 80%) of the titled compound.

(5) Synthesis of (S)-1,1'-Binaphthalene-2,2'-diyldioxychlorophosphine:

In a 50 ml flask equipped with a reflux condenser were charged 4.94 g (17.3 mmol) of (S)-1,1'-bi-2-naphthol and 113 g (830 mmol) of phosphorus trichloride in an argon stream, and the mixture was heated at reflux for 4 hours, followed by cooling to room temperature. The unreacted phosphorus trichloride was removed by distillation under reduced pressure to give 5.56 g (percent yield: 92%) of the titled compound as a white crystal.

(6) Synthesis of (R)-2-Diphenylphosphino-5,5',6,6',7,7',8, 8'-octahydro- 1,1'-binaphthalene-2'-yloxy-((S)-1,1'-binaphthalene- 2,2'-diyldioxy)phosphine:

In a 100 ml flask, 0.438 g (0,946 mmol) of (R)-2-dihenylphosphino- 2'-hydroxy-5,5',6,6',7,7',8,8'-octahydro-1,1'-binaphthyl and 662 mg (1.89 mmol) of (S)-1,1'-binaphthalene- 2,2'-diyldioxychlorophosphine were dissolved in 30 ml of ethyl ether, and 191 mg (1.89 mmol) of triethylamine was added to the solution at 0° C. The mixture was stirred at room temperature for 15 hours, and 20 ml of water was added thereto to cease the reaction.

After liquid-liquid separation, the organic layer separated was dried over anhydrous magnesium sulfate, and the solvent was removed by distillation to obtain a crude product. Purification by silica gel column chromatography using a 1:1 mixture of hexane and benzene as a developing solvent yielded 719.4 mg (percent yield: 98%) of (R)-2-diphenylphosphino- 5,5',6,6',7,7',8,8'-octahydro-1,1binaphthalen-2,2-yloxy-((S)- 1,1'-binaphthalene-2,2'-diyldioxy)phosphine (hereinafter referred to as (R,S) -OcH-BINAPHOS) as a white crystal. $^{31}$p-NMR (CDCl$_3$) δ:

−14.8 (d, J=42.7 Hz), 146.8 (d, J=42.7 Hz)

EXAMPLE 10

Synthesis of (R)-2-Diphenylphosphino-5,5',6,6',7,7',8,8'-octahydro- 1,1'-binaphthalen-2'-yloxy-((S)-5,5',6,6',7,7',8, 8'-octahydro- 1,1'-binaphthalene-2,2'-diyldioxy)phosphine (1) Synthesis of (S)-5,5'6,6,7,7',8,8'-Octahydro-1,1'-binaphthalene- 2,2'-diyldioxychlorophosphine:

In a 50 ml flask were charged 5.12 g (17.3 mmol) of (S)-5,5',6,6',7,7',8,8'-octahydro-1,1'-bi-2-naphthol and 113 g (830 mmol) of phosphorus trichloride in an argon stream, and the mixture was heated at reflux for 4 hours, followed by cooling to room temperature. The unreacted phosphorus trichloride was removed by distillation under reduced pressure to give 5.7 g (percent yield: 92%) of the titled compound as a white crystal.

(2) Synthesis of (R)-2-Diphenylphosphino-5,5',6,6',7,7',8, 8'-octahydro- 1,1'-binaphthalen-2'-yloxy- ((S)- 5,5',6,6',7,7', 8,8'-octahydro-1,1'-binaphthalene-2,2'-diyldioxy)phosphine (hereinafter referred to as (R,S)-(OcH)$_2$-BINAPHOS):

(R,S)-(OcH)$_2$-BINAPHOS) was obtained in a percent yield of 91% in the same manner as in Example 9-(6), except for replacing (S)-1,1'-binaphthalene-2,2 '-diyldioxychlorophosphine with (S)-5,5',6,6',7,7',8,8'-octahydro-1,1'-binaphthalene- 2,2'-diyldioxychlorophosphine.

$^{31}$p-NMR (CDCl$_3$) δ:

−14.6 (d, J=39.7 Hz), 138.2 (d, J=39.7 Hz)

EXAMPLE 11

Synthesis of Rh((R,S)-OcH-BINAPHOS) (acac)

In a 20 ml Schlenk's tube were charged 19.4 mg (0.025 mmol) of (R,S) -OcH-BINAPHOS and 6.5 mg (0.025 mmol) of Rh(CO)$_2$(acac) and dissolved with 5 ml of methylene chloride. After stirring at room temperature for 5 minutes, the solvent was removed by distillation under reduced pressure to obtain Rh((R,S)-OcH-SINAPHOS) (acac) as a yellow solid in a percent yield of 100%.

$^{31}$P-NMR (CDCl$_3$) δ:

46.2 (dd, J$_{p-p}$=82.4 Hz, H$_{Rh-p}$=174.0 HZ) , 160.7 (dd, J$_{Rh-p}$=331.0 HZ )

EXAMPLE 12

Synthesis of Rh((R,S)-(OcH)$_2$-BINAPHOS) (acac).

The titled compound was obtained in a percent yield of in the same manner as in Example 11, except for replacing (R,S) -OcH-BINAPHOS with (R,S)-(OcH)$_2$-BINAPHOS.

$^{31}$P-NMR (CDCl$_3$) δ:

48.3 (dd, J$_{p-p}$=83.9 Hz, J$_{Rh-p}$=174.0 Hz) , 161.8 (dd, J$_{Rh-p}$=331.1 Hz)

EXAMPLE 13

Complexes shown in Table 3 below were prepared in the same manner as in the foregoing Examples.

TABLE 3

| | L | |
|---|---|---|
| | 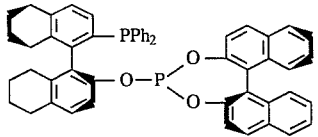 | 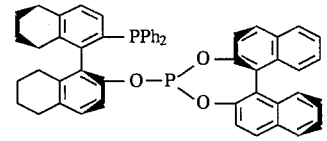 |
| | (S,R)-OcH-BINAPHOS<br>$^{31}$P-NMR δ:<br>−14.8(d, J=40Hz)<br>146.8(d, J=40Hz) | (S,S)-OcH-BINAPHOS<br>$^{31}$P-NMR δ:<br>−14.0(br, s)<br>146.9(d, J=10Hz) |
| Metal | | |
| Pd | [PdCl$_2$(L)]<br>$^{31}$P-NMR δ:<br>24.3(br, s)<br>131.2(d, J=21Hz) | [PdCl$_2$(L)]<br>$^{31}$P-NMR δ:<br>27.1(br, s)<br>126.5(d, J=18Hz) |
| Ir | [Ir(COO)(L)]BF$_4$<br>$^{31}$P-NMR δ:<br>17.9(d, J=38Hz)<br>18.8(d, J=39Hz)<br>145.6(d, J=38Hz)<br>147.2(d, J=39Hz) | |

| L | |
|---|---|
| 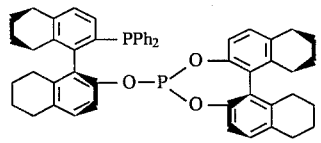 | 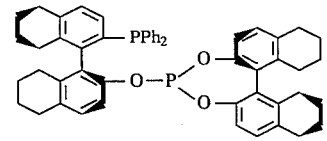 |
| (S,R)-(OcH)$_2$-BINAPHOS<br>$^{31}$P-NMR δ:<br>−14.6(d, J=41Hz) | (S,S)-(OcH)$_2$-BINAPHOS<br>$^{31}$P-NMR δ:<br>−13.4(br, s) |

TABLE 3-continued

| Metal | 138.2(d, J=39Hz) | 139.1(d, J=8Hz) |
|---|---|---|
| Pd | [PdCl$_2$(L)]<br>$^{31}$P-NMR δ:<br>23.9(q, J=12Hz)<br>124.8(d, J=24Hz) | [PdCl$_2$(L)]<br>$^{31}$P-NMR δ:<br>27.1(br, s)<br>119.0(d, J=19Hz) |
| Ir | [Ir(COO)(L)]BF$_4$<br>$^{31}$P-NMR δ:<br>−15.2(d, J=37Hz)<br>115.6(d, J=31Hz) | |

L and COD are as defined above.

REFERENCE EXAMPLE 4

Asymmetric Hydroformylation of Vinyl Acetate

In a 50 ml autoclave were put 761 mg (8.84 mmol) of vinyl acetate, 8.6 mg (0.00884 mmol) of Rh((R,S)-OcH-BINAPHOS)(acac), and 8.3 ml of benzene. Hydrogen and carbon monoxide were introduced into the autoclave to a total pressure of 100 atm with the hydrogen pressure being 50 atm, and the mixture was stirred at 60° C. for 44 hours to obtain a mixture of 2-acetoxypropanal and 3-acetoxypropanal at a ratio of 88.6:11.4 as determined by $^1$H-NMR. The conversion of vinyl acetate was 72% as determined by $^1$H-NMR. The resulting aldehyde was converted to the corresponding carboxylic acid by Jones oxidation and analyzed by optically active gas chromatography (CHROMPACK, CP-Cyclodextrin β-236-m-19; measured at 145° C.). As a result, the optical purity of the 2-acetoxypropanal was found to be 90% ee.

REFERENCE EXAMPLE 5

Hydroformylation of Styrene

In a 50 ml autoclave were charged 1.04 g (10 mmol) of styrene, 9.8 mg (0.01 mmol) of Rh((R,S)-OcH-BINAPHOS)(acac), and 10 ml of benzene. Hydrogen and carbon monoxide were introduced into the autoclave to a total pressure of 100 atm with the hydrogen pressure being 50 atm, and the mixture was stirred at 60° C. for 100 hours. After completion of the reaction, the temperature was lowered to room temperature, and the pressure was relieved. The solvent was removed by distillation to obtain a mixture of 2-phenylpropanal and 3-phenylpropanal. The mixing ratio and the optical purity of product were measured in the same manner as in Reference Example 4. As a result, the conversion of styrene was 100%, the 2-phenylpropanal to 3-phenylpropanal ratio was 92.4:7.6, and the optical purity of the 2-phenylpropanal was 92.7% ee.

REFERENCE EXAMPLE 6

Hydroformylation of Styrene

Styrene was hydroformylated in the same manner as in Reference Example 5, except for using Rh((R,S)-(OcH)$_2$-BINAPHOS)(acac) as a catalyst. As a result, the conversion of styrene was 84%, and the product was a mixture of 91.7% of 2-phenylpropanal and 8.3% of 3-phenylpropanal. The optical purity of the 2-phenylpropanal was 88.9% ee.

As described above, the transition metal-phosphine complex according to the present invention can be used as a catalyst for asymmetric synthesis to produce a purposed compound having a desired absolute configuration at a high optical purity in a high yield.

Examples of the Stereoselective Hydroformylation Aspect of the Invention

EXAMPLE 14

Synthesis of (R)-2,2'-bis)trifluoromethanesulfonyloxo)-1,1'-binaphthyl (hereinafter called "Compound I"):

In a 100-ml flask, 5 g (17.4 mmol) of (R)-1,1'-bi-2-naphthol, 5.58 g (52.2 mmol) of 2,6-lutidine and 0.955 g (7.83 mmol) of 4-dimethylaminopyridine (Wako) were dissolved in 26 ml of methylene chloride, to which 14.7 g (52.2 mmol) of trifluoromethanesulfonic anhydride was added at 0° C. The contents were stirred for 23 hours at room temperature to complete the reaction. After completion of the reaction, the solvent was distilled off, and the residue was then purified by column chromatography on silica gel making use of methylene chloride as a developing solvent to obtain 9.56 g (yield: 100%) of (R)-2,2'-bis(trifluoromethanesulfonyloxy)-1,1'-binaphthyl.

Synthesis of (R)-2-diphenylphosphinyl-2'-trifluoromethanesulfonyloxy-1,1'-binaphthyl (hereinafter called "Compound II"):

In a 100-ml 4-necked flask, 2.74 g (4.98 mmol) of Compound I and 1.99 g (9.82 mmol) of diphenylphosphine oxide were dissolved in 20 ml of dimethylsulfoxide in an argon stream, to which 110 mg (0,491 mmol) of palladium acetate, 203 mg (0,491 mmol) of 1,3-bis(diphenylphosphino)propane, 5.1 ml of ethyldiisopropylamine and 3.3 mg (0,491 mmol) of sodium formate were added to stir them for 20 minutes at room temperature. Thereafter, the resultant solution was stirred for 19 hours at 90° C. and then cooled back to room temperature. The solution was combined with 250 ml of ether and 150 ml of water, and the mixture was stirred to separate an organic layer and an aqueous layer. After the separation, the organic layer was washed four times with 125 ml of water, twice with 125 ml of 5% diluted hydrochloric acid, twice with 50 ml of water, once with 125 ml of a saturated aqueous solution of sodium hydrocarbonate and lastly with 125 ml of a brine. The thus-washed organic layer was dried on anhydrous magnesium sulfate, and the solvent was distilled off. The residue was then purified by column chromatography on silica gel making use of a 3:1 (solvent ratio, the same shall apply hereinafter) mixture of toluene and acetonitrile as a developing solvent, thereby obtaining 2.51 g (yield: 83%) of the title compound.

Synthesis of (R)-2-diphenylphosphino-2'-hydroxy-1.1'-binaphthyl (hereinafter called "Compound III"):

In a 50-ml 3-necked flask, 400 mg (0.664 mmol) of Compound II was dissolved in 22 ml of xylene, to which 1.21 g (12 mmol) of triethylamine and 1.62 g (12 mmol) of trichlorosilane were added. The resulting mixture was stirred for 17 hours at 120° C. After the reaction mixture was cooled back to room temperature, 4.4 ml of 35% aqueous sodium hydroxide was carefully added thereto, and the mixture was stirred further for 2 hours, followed by separation of an organic layer and an aqueous layer. After the separation, the organic layer was washed twice with 30 ml of a brine and then dried over anhydrous magnesium sulfate, and the solvent was distilled off under reduced pressure, thereby obtaining a crude product. The crude product was dissolved in 7 ml of tetrahydrofuran, to which a solution of 335 mg (7.98 mmol) of lithium hydroxide in 2.4 ml of water was added. The resulting mixture was stirred for 15 hours at room temperature, to which 50 ml of ether and 15 ml of 5% diluted hydrochloric acid were added to separate an organic layer and an aqueous layer. After the organic layer was washed twice with water, it was dried over anhydrous magnesium sulfate, and the solvent was distilled off. The residue was then purified by column chromatography on silica gel making use of a 5:1 mixture of hexane and ethyl acetate as a developing solvent, thereby obtaining 153 mg (yield: 51%) of the title compound.

Synthesis of (S)-1,1'-binaphthalene-2,2'-diyldioxychlorophosphine (hereinafter called "Compound IV"):

A 50-ml flask was charged with 4.94 g (17.3 mmol) of (S)- 1,1'-bi-2-naphthol and 113 g (0.83 mol) of phosphorus trichloride in an argon stream and the mixture was refluxed for 4 hours. Thereafter, the reaction mixture was cooled back to room temperature, and unreacted phosphorus trichloride was distilled off under reduced pressure, thereby obtaining 5.56 g (yield: 92%) of the title compound as colorless crystals.

Synthesis of (R)-2-diphenylphosphino-1,1'-binaphthalene- 2'-yloxy((S)-1.1'-binaphthalene-2,2'-diyldioxy)phosphine [hereinafter abbreviated as "(R,S)-BINAPHOS"]:

In a 100-ml flask, 430 mg (0.946 mmol) of Compound III and 662 mg (1.89 mmol) of Compound IV were dissolved in 30 ml of ether, to which 191 mg (1.89 mmol) of triethylamine was added at 0° C. After the mixture was stirred for 15 hours at room temperature, 20 ml of water was added to stop the reaction. After separating an organic layer and an aqueous layer, the organic layer was dried on anhydrous magnesium sulfate, and the solvent was distilled off, thereby obtaining a crude product. The crude product was purified by column chromatography on silica gel making use of a 1:1 mixture of hexane and dichloromethane as a developing solvent, thereby obtaining 712 mg (yield: 98%) of (R,S)-BINAPHOS as white crystals. $^{31}$p-NMR (CDCl$_3$) δ: −14.6(d,J=29.0 Hz), 144.7(d,J=29.0 Hz).

Asymmetric hydroformylation reaction of vinyl acetate:

A 50 ml autoclave was charged with 1,301 g (15.13 mmol) of vinyl acetate, 9.8 mg (0.0378 mmol) of Rh(CO)$_2$(acac) as a catalyst precursor, 58 mg (0.0755 mmol) of (R,S)-BINAPHOS as an optically active phosphine and 14 ml of benzene. The contents were stirred at 60° C. for 112 hours under a hydrogen pressure of 50 atm and a carbon monoxide pressure of 50 atm. The determination of conversion of vinyl acetate and the analysis of the reaction products were conducted by gas chromatography (10% SE-30 on Chromosorb W 80–100 mesh packed in a 5 mm×2 m glass column), and the optical purities of the products were determined by gas chromatography (Astec Chiraldex B-PH). As a result, it was found that compounds produced by this reaction were a mixture of 90% of 2-acetoxypropanal and 10% of 3-acetoxypropanal, and the conversion was 98%. 2-Acetoxypropanal was then distilled to determine its optical purity. As a result, it was found to be 90% ee. This compound was then caused to undergo Jones oxidation to prepare 2-acetoxypropionic acid. Its optical rotation was measured. As a result, it was confirmed that the compound is (S)-(−)-2-acetoxypropionic acid.

EXAMPLE 15

Synthesis of (R)-2-(diphenylphosphino)-1,1'-binaphthalene- 2'-yloxy((R)-1,1'-binaphthalene-2,2'-diyldioxy)phosphine [hereinafter abbreviated as "(R,R)BINAPHOS"]:

A 100-ml flask was charged with 30 ml of ether, to which 209 mg (0.46 mmol) of Compound III and 322 mg (0.92 mmol_ of (R)-1,1'-binaphthalene-2,2'-diyldioxychlorophosphine were added to dissolve them in ether. To the solution, 191 mg (1.89 mmol) of triethylamine was added at 0° C. Thereafter, the same procedure as in (R,S)-BINAPHOS was followed to obtain 353 mg (yield: 96.3%) of the title compound. $^{31}$p-NMR (CDCl$_3$) δ: −18.0(d,J=9.2 Hz), 140.5(d,J=9.2 Hz).

Synthesis of Rh((R,R)-BINAPHOS) (acac):

A 20-ml Schlenk's tube was charged with 0.025 mmol of (R,R)-BINAPHOS and 6.5 mg (0.025 ml) of Rh(CO)$_2$(acac) (acac means acetylacetonate, the same shall apply hereinafter) to dissolve them in 5 ml of methylene chloride. After the reaction mixture was stirred for 5 minutes at room temperature, the solvent was distilled off under reduced pressure to obtain 63 mg (yield: 99%) of Rh(R,R)-BINAPHOS) (acac).

$^{31}$p-NMR (CDCl$_3$) δ: 51.9(dd,J$^{p-p}$=80.8 Hz, J$_{Rh-p}$=178.4 HZ), 152.5 (dd,J$_{Rh-p}$=335.1 Hz)

Asymmetric hydroformylation reaction of vinyl acetate:

The same procedure as in Example 14 was followed except that Rh(R,R)-BINAPHOS)(acac) was used as a catalyst, and the reaction was conducted for 37 hours at 50° C., thereby obtaining a mixture of 92% of 2-acetoxypropanal and 8% of 3-acetoxypropanal. The conversion was 46%. The optical purity of 2-acetoxypropanal after distillation was determined in the same manner as in Example 14, and was found to be 73% ee. This compound was then oxidized by Jones oxidation to prepare 2-acetoxypropionic acid. Its optical rotation was measured. As a result, it was confirmed that the compound is (S)-)(−)-2-acetoxypropionic acid.

EXAMPLE 16

A 50-ml autoclave was charged with 3.06 g (29.4 mmol) of styrene, 3.7 mg (0.0143 mmol) of Rh(CO)2(acac), 44 mg (0.0573 mmol) of (S,R)-BINAPHOS and 1 ml of benzene. The contents were stirred at 60° C. for 43 hours under a hydrogen pressure of 50 atm and a carbon monoxide pressure of 50 atm. After completion of the reaction, the reaction mixture was cooled back to room temperature, and the gases under pressure were removed. Thereafter, the reaction mixture was directly analyzed by $^1$H-NMR. As a result, it was found that the conversion of styrene was at least 99%, and a mixture of 88% of 2-phenylpropanal and 12% of 3-phenylpropanal as reaction products was obtained in an amount of 1.273 g. No other products were observed. After distilling, the thus-obtained 2-phenylpropanal was oxidized by Jones oxidation to prepare 2-phenylpropionic acid. Its optical purity was determined. As a result, it was confirmed that the compound is (S)-(+)-2-phenylpropionic acid having an optical purity of 94% ee.

EXAMPLES 17–22

The same procedure as in Example 14 was followed except that the substrate, the phosphine as a ligand, the amount of the rhodium compound, and the reaction temperature and time were changed as shown in Table 4, thereby obtaining results corresponding to the following reaction:

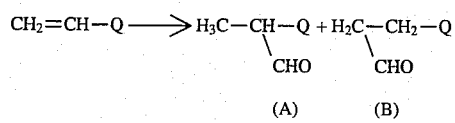

The results are shown in Table 4.

(2) Preparation of (±)-3,3'-Dichloro-2,2',4,4'-tetramethyl-6,6'-bis(trifluoromethanesulfonyloxy)biphenyl (hereinafter referred to as compound (B)):

In a flask, 6.22 g (20.0 mol) of compound (A) obtained in (1) above, 4.72 g (44.0 mmol) of 2,6-lutidine, and 732 mg (6.00 mmol) of 4-dimethylaminopyridine were dissolved in 30 ml of dichloromethane in an argon stream, and 12.4 g (44.0 mmol) of trifluoromethanesulfonic acid anhydride was added to the solution at 0° C., followed by allowing to react

TABLE 4

| Ex. | Q | S/C | Phosphine ligand | Temperature (°C.) | Time (hr) | Conversion (%) | (A)/(B) | % ee of (A) | Configuration and optical rotation |
|---|---|---|---|---|---|---|---|---|---|
| 17 | i-Bu—C6H4— | 300 | (S,R)-BINAPHOS | 60 | 66 | At least 99 | 88/12 | 92 | S-(+) |
| 18 | Me—C6H4— | 1000 | " | 60 | 20 | 97 | 86/14 | 95 | (+) |
| 19 | MeO—C6H4— | 1000 | " | 60 | 34 | At least 99 | 87/13 | 88 | (+) |
| 20 | Cl—C6H4— | 1000 | " | 60 | 34 | At least 99 | 87/13 | 93 | (+) |
| 21 | phthalimido-N— | 300 | " | 60 | 90 | 98 | 89/11 | 85 | R-(+) |
| 22 | n-Bu | 1000 | (R,S)-BINAPHOS | 30 | 93 | 90 | 24/76 | 75 | R-(−) |

S/C means a ratio of the substrate to the rhodium compound.
i-Bu denotes a butyl group.

EXAMPLE 23

Preparation of (S)-3,3'-Dichloro-2,2',4 4'-tetramethyl-6-diphenylphosphinobiphenyl-6'-yloxy((R)-1,1'-binaphthalene- 2,2'-diyldioxy)phosphine and (R)-3,3'-Dichloro-2,2',4 4'-tetramethyl-6-diphenylphosphinobiphenyl-6'-yloxy((R)-1,1'-binaphthalene-2,2'-diyldioxy)phosphine (1) Preparation of (±)-3,3'-Dichloro-2,2',4,4'-tetramethyl-biphenyl-6,6'-diol (hereinafter referred to as compound (A)):

In a flask were charged 10.1 g (70.0 mmol) of 4-chloro-3,5-xylenol and 37.8 g (140 mmol) of iron trichloride hexahydrate, and the mixture was allowed to react at 80° C. for 16 hours. After completion of the reaction, the reaction mixture was treated with 300 ml of in hydrochloric acid and extracted with three 250 ml portions of dichloromethane. The organic layer was washed successively with 500 ml of a saturated sodium hydrogencarbonate aqueous solution and 500 ml of brine, concentrated, and recrystallized from hexane/chloroform to obtain 3.32 g (percent yield 30%) of compound (A).

Melting point: 231°–233° C.

$^1$H-NMR (CDCl$_3$) δ:

2.05 (s, 6H), 2.41 (s, 6H), 4.57 (s, 2H), 6.84 (s, 2H)

at that temperature for 1 hour. After completion of the reaction, the solvent was removed under reduced pressure, and the residue was purified by column chromatography (hexane/chloroform=1:1 by volume) to obtain 10.9 g (percent yield 95%) of compound (S).

Melting point: 90°–91° C.

$^1$H-NMR (CDCl$_3$) δ: 2.14 (s, 6H), 2.50 (s, 6H), 7.17 (s, 2H)

(3) Preparation of (±-3,3'-Dichloro-2,2',4,4'-tetramethyl-6-diphenylphosphinyl-6-trifluoromethanesulfonyloxy-biphenyl (hereinafter referred to as compound (C)):

In a flask, 11.44 g (19.9 mmol) of compound (B) obtained in (2) above and 8.05 g (39.8 mmol) of diphenylphosphine oxide and 223 mg (0.99 mmol) of palladium acetate were dissolved in 980 ml of dimethyl sulfoxide in an argon stream. To the solution were added 821 mg (1.99 mmol) of 1,3-bis(diphenylphosphino)propane and 15.3 ml of diisopropylamino over 20 minutes, followed by stirring at 90° C. for 60 hours. After completion of the reaction, 120 ml of water was added to the reaction mixture, and the mixture was extracted with two 250 ml portions of ethyl ether. The organic layer was washed successively with 200 ml of water, 200 ml of 1N hydrochloric acid, 200 ml of a saturated sodium hydrogencarbonate aqueous solution, and 200 ml of brine and dried over magnesium sulfate. Purification by column chromatography (hexane/ethyl acetate=1:1 by volume) gave 7.77 g (percent yield 62%) of compound (C).

Melting point: 159°–160° C.

$^{31}$P-NMR (CDCl$_3$) δ: 27.75

(4) Preparation of (±)-3,3'-Dichloro-2,2',4,4'-tetramethyl-6 -diphenylphosphino-6'-hydroxybiphenyl (hereinafter referred to as compound (D)):

In a flask, 7.32 g (11.7 mmol) of compound (C) obtained in (3) above and 47.2 g (467 mmol) of triethylamine were dissolved in 400 ml of xylene. To the solution was added dropwise 63.3 g (467 mmol) of trichlorosilane at 0° C., followed by stirring at 120° C. for 35 hours. To the solution was carefully added dropwise 200 ml of a saturated sodium hydroxide aqueous solution at 0° C., followed by stirring at 60° C. for 2 hours. After completion of the reaction, the reaction mixture was extracted with two 150 ml portions of toluene. The organic layer was washed with 400 ml of water and then with 300 ml of brine and dried over magnesium sulfate. The solvent was removed under pressure. The residue weighing 7.46 g was dissolved in 130 ml of tetrahydrofuran in a flask, and 44 ml of an aqueous solution of 5.87 g (140 mmol) of lithium hydroxide monohydrate was added thereto, followed by stirring at 30° C. for 15 hours. After completion of the reaction, 200 ml of 1N hydrochloric acid was added to the reaction mixture, and the mixture was extracted with two 200 ml portions of ethyl ether. The resulting organic layer was washed successively with 300 ml of water and 250 ml of brine and dried over magnesium sulfate. The solvent was removed under reduced pressure, and the residue was purified by column chromatography (hexane/ethyl acetate=12:1 to 3:1 by volume) to obtain 5.05 g of compound (D) in 90% yield based on compound (C).

Melting point: 71°–79° C.

$^{31}$P-NMR (CDCl$_3$) δ: –13.37

(5) Preparation of (R)-1,1'-Binaphthalene-2,2'-diyldioxychlorophosphine (hereinafter referred to as compound (E)) and (S)-1,1'-binaphthalene-2,2'-diyldioxychlorophosphine (hereinafter referred to as compound (F)):

In 50 ml-flask equipped with a reflux condenser were charged 4.94 g (17.3 mmol) of (R)-1,1'-bi-2-naphthol and 104 g (757 mmol) of phosphorus trichloride in an argon stream, and the mixture was refluxed for 17 hours. After cooling to room temperature, the unreacted phosphorus trichloride was removed by distillation under reduced pressure. The residue was subjected twice to azeotropic distillation together with 50 ml of toluene under reduced pressure. The residue was dissolved in benzene, and the solution was dried under reduced pressure to obtain 5.56 g (percent yield 92%) of compound (E) as a white solid.

$^{31}$P-NMR (CDCl$_3$) δ: 178.8

Compound (F) was prepared quantitatively in the same manner as for compound (E).

(6) Preparation of (S)-3,3'-Dichloro-2,2',4,4'-tetramethyl-6 -diphenylphosphinobiphenyl-6'-yloxy((R)-1,1'-binaphthalene- 2,2'-diyldioxy)phosphine (hereinafter referred to as (S,R)-biphemphos) and (R)-3,3'-dichloro-2,2',4,4'-tetramethyl-6 -diphenylphosphinobiphenyl-6'-yloxy((R)-1,1'-binaphthalene- 2,2'-diyldioxy)phosphine (hereinafter referred to as (R,R)-biphemphos):

In 40 ml of toluene were dissolved 756 mg (1.58 mmol) of compound (D) and 1336 mg (3.81 mmol) of compound (E) in a flask, and 386 mg (3.81 mmol) of triethylamine was added thereto at 0° C. After stirring the mixture at room temperature for 42 hours, 50 ml of water was added thereto to cease the reaction. To the reaction mixture was added 50 ml of ethyl ether for liquid-liquid separation, and the organic layer was washed successively with two 80 ml portions of water and 80 ml of brine, and dried over anhydrous magnesium sulfate. The solvent was removed under reduced pressure, and the resulting crude product was purified by column chromatography (hexane/dichloromethane=20:1 to 3:1 by volume) to obtain 395 mg (percent yield 32%) of (S,R)-biphemphos and 259 mg (percent yield 21%) of (R,R)-biphemphos. (S,R)-biphemphos:

Melting point: 155°–162° C.

$[α]_D^8$: –281° (c=1.0, toluene)

$^{31}$P-NMR (toluene-d$_8$) δ: –13.4 (d, $J_{p-p}$=35.14 Hz), 146.7 (d)

Thin layer chromatography (TLC):

Rf=0.47 (hexane/dichloromethane=1:1 by volume) (R,R)-biphemphos:

Melting point: 153°–159° C.

$[α]_D^2$: –252° (c=1.0, toluene)

$^{31}$P-NMR (toluene-d$_8$) δ: –12.6 (d, $J_{p-p}$=12.2 Hz), 145.8 (d)

TLC: Rf=0.42 (hexane/dichloromethane=1:1 by volume)

EXAMPLE 24

(R)-3,3'-Dichloro-2,2',4,4'-tetramethyl-6 -diphenylphosphinobiphenyl-6'-yloxy((S)-1,1'-binaphthalene- 2,2'-diyldioxy) phosphine (hereinafter referred to as (R,S)-biphemphos) and (S)-3,3'-dichloro-2,2',4,4'-tetramethyl-6 -diphenylphosphinobiphenyl-6'-yloxy((S)-1,1'-binaphthalene- 2,2'-diyldioxy) phosphine (hereinafter referred to as (S,S)-biphemphos), which are isomers of the products of Example 23. were obtained in the same manner as in Example 23.

(R,S)-biphemphos:

Melting point: 153°–158° C.

273° (c=1.0, toluene)

$^{31}$P-NMR (toluene-d$_8$) δ: –13.3 (d, $J_{p-p}$=36.6 Hz), 146.8 (d)

TLC: Rf=0.47 (hexane/dichloromethane=1:1 by volume) (S,S)-biphemphos:

Melting point: 147°–151° C.

$α_D^2$: 253° (c=1.0, toluene)

$^{31}$P-NMR (toluene-d$_8$) δ: –12.6 (d, $H_{p-p}$=13.8 Hz), 145.8 (d)

TLC: Rf=0.42 (hexane/dichloromethane=1:1 by volume)

EXAMPLE 25

Preparation of (R) -3,3',4,4',5,5'-hexamethyl-6 -diphenylphosphinobiphenyl-6'-yloxy ((S) -1,1'-binaphthalene-2,2'-diyldioxy)phosphine and (S)-3,3',4,4',5,5'-hexamethyl-6 -diphenylphosphinobiphenyl-6-yloxy ((S) -1,1'-binaphthalene-2,2'-diyldioxy)phosphine (1) Preparation of (±)-2,2',3 3',4,4'-hexamethylbiphenyl-6,6'-diol (hereinafter referred to as compound (A"):

Compound (A") was prepared from 3,4,5-trimethylphenol in 53% yield by the same method of the synthesis of compound (A).

$^1$H-NMR (CDCl$_3$) δ: 1.92 (s,6H), 2.16 (s,6H), 2.31 (s,6H), 4.50 (s,2H), 6.74 (s,2H)

TLC: Rf=0.28 (dichloromethane)

(2) Preparation of (+)-2,2',3,3',4,4'-hexamethyl-6,6'-bis (trifluoromethanesulfonyloxy) biphenyl (hereinafter referred to as compound (B")):

Compound (B") was prepared from compound (A") in 90% yield by the same method of the synthesis of compound (B).

$^1$H-NMR (CDCl$_3$) δ: 2.00 (s,6H), 2.24 (s,6H), 2.38 (s,6H), 7.04 (s,2H)

TLC: Rf=0.31 (hexane/dichloromethane=1:1 by volume)

(3) Preparation of (+)-2,2',3,3',4,4'-hexamethyl-6 -diphenylphosphinyl-6'- trifluoromethanesulfonyloxybiphenyl (hereinafter referred to as compound (C")):

Compound (C") was also prepared from compound (B") in 77% yield by the same method of the synthesis of compound (C).

$^{31}$P-NMR (CDCl$_3$) δ: 28.2 0

TLC: Rf=0.70 (ethylacetate)

(4) Preparation of (+)-2,2',3,3',4,4'-hexamethyl-6 -diphenylphosphino-6'-hydroxybiphenyl (hereinafter referred to as compound (D")):

Compound (D") was prepared from compound (C") in 74% yield by the same method of the synthesis of compound (D).

$^{31}$P-NMR (CDCl$_3$) δ: –13.46

TLC: Rf=0.6 8 (hexane/ethylacetate=7:3)

(5) Preparation of (R)-3,3',4,4',5,5'-hexamethyl-6 -diphenylphosphinobiphenyl-6'-yloxy ((S)-1,1'-binaphthalene-2,2'-diyldioxy) phosphine (hereinafter referred to as (R,S)-Me-biphemphos) and (S)-3,3',4,4',5,5'-hexamethyl-6 -diphenylphosphinobiphenyl-6'-yloxy ((S)-1,1'-binaphthalene-2,2'-diyldioxy) phosphine (hereinafter referred to as (S,S)-Me-biphemphos)

(R,S)-Me-biphemphos and (S,S)-Me-biphemphos were prepared by the same method of the synthesis of (R,R)-biphemphos and (S,R)-biphemphos from compound (D") and compound (F).

(R,S)-Me-biphemphos:

$^{31}$P-NMR (benzene-d$_6$) δ: –13.3 (d,H$_{p-p}$=39.6 Hz), 147.6 (d)

TLC: Rf=0.60 (hexane/dichloromethane=1:1)

(S,R) -Me-biphemphos:

$^{31}$P-NMR (benzene-d$_6$) δ: –12.9 (d,H$_{p-p}$=13.8 Hz), 147.3 (d)

TLC: Rf=0.53 (hexane/dichloromethane=1:1)

EXAMPLE 26

Preparation of (R)-2-Diphenylphosphino-1,1'-biphenyl-2'-yloxy((R)-1,1'-binaphthalene-2,2'-diyldioxy)phosphine and (S)-2-Diphenylphosphino-1,1'-biphenyl-2'-yloxy((R)-1,1'-binaphthalene-2,2'-diyldioxy)phosphine (1) Preparation of 2,2'-bis(trifluoromethanesulfonyloxy)biphenyl (hereinafter referred to as compound (B')):

In the same manner as in Example 23-(2), compound (B') was obtained in 96% yield.

Melting point: 33°–34° C.

TLC: Rf=0.67 (hexane/ethyl acetate=7:3 by volume)

(2) Preparation of 2-diphenylphosphinyl-2'-trifluoromethanesulfonyloxybiphenyl (hereinafter referred to as compound (C')):

In the same manner as in Example 23-(3), compound (C') was obtained in 79% yield.

Melting point: 123°–124° C.

$^{31}$P-NMR (CDCl$_3$) δ: 27.78

$^{19}$F-NMR (CDCl$_3$) δ: –6.05

(3) Preparation of 2-diphenylphosphino-2'-hydroxybiphenyl (hereinafter referred to as compound (D')):

In the same manner as in Example 23-(4), compound (D') was obtained in 60% yield.

Melting point: 122°–123° C.

$^{31}$P-NMR (CDCl$_3$) δ: –12.01

(4) Preparation of (R)-2-diphenylphosphino-1,1'-biphenyl-2'-yloxy((R)-1,1'-binaphthalene-2,2'-diyldioxy)phosphine (hereinafter referred to as (R,R)-H-biphemphos) and (S)-2 -diphenylphosphino-1,1'-biphenyl-2'-yloxy((R)-1,1'-binaphthalene-2,2'-diyldioxy)phosphine (hereinafter referred to as (S,R)-H-biphemphos):

In the same manner as in Example 23-(6), 871 mg (percent yield 62%) of a mixture of (R,R)-H-biphemphos and (S,R)-H-biphemphos was obtained at an (S,R)-H-biphemphos/(R,R)-H-biphemphos ratio of 55:45.

Mixture:

Melting point: 150°–156° C.

$α_D^2$: 324° (c=1.0, toluene)

(S,R)-H-biphemphos:

$^{31}$P-NMR (toluene-d$_8$) δ: –11.9 (d, H$_{p-p}$=35.1 Hz), 146.77 (d)

(R,R)-H-biphemphos:

$^{31}$P-NMR (toluene-d$_8$) δ: –11.5 (d, H$_{p-p}$=21.4 Hz), 146.81 (d)

EXAMPLE 27

Synthesis of (R)-2-Diphenylphosphino-5,5',6,6',7,7',8,8'-octahydro- 1,1'-binaphthalen-2'-yloxy-((S)-1,1'-binaphthalene- 2,2'-diyldioxy) phosphine (1) Synthesis of (R)-5,5',6,6',7,7',8,8'-octahydro-1,1'-bi-2-naphthol:

In a 200 ml autoclave were charged 3.00 g (10.5 mmol) of (R)-2,2 '-dihydroxy-1,1'-binaphthyl, 360 mg of platinum dioxide, and 75 ml of acetic acid, and the mixture was stirred at 5° C. for 18 hours at a hydrogen pressure of 3 atm and then at 18° C. for 7 days at a hydrogen pressure of 10 atm. Ethyl acetate was added thereto, and the reaction mixture was filtered through Celite. Water was added to the filtrate for separation, and the separated organic layer was washed twice with a saturated sodium hydrogencarbonate aqueous solution, followed by separation. The organic layer was dried over magnesium sulfate, and the solvent was removed under reduced pressure to obtain 3.03 g (percent yield 98%) of the titled compound. Optical purity: ≧99 %ee.

(2) Synthesis of (R)-2,2'-bis(trifluoromethanesulfonyloxy)- 5,5',6,6',7,7',8,8'-octahydro-1,1'-binaphthyl:

In a 50 ml four-necked flask were charged 26 ml of methylene chloride, 5.15 g (17.4 mmol) of (R)- 5,5',6,6',7,7',8,8'-octahydro-1,1'-bi-2-naphthol, 5.58 g ( 52.2 retool) of 2,6-toluidine, and 0. 955 g (7.83 retool) of 4-dimethylaminopyridine. To the solution was added 14.7 g (52.2 mmol) of trifluoromethanesulfonic acid anhydride at 0° C., followed by stirring at room temperature for 23 hours. After completion of the reaction, the solvent was removed under reduced pressure, and the residue was purified by column chromatography on silica gel using methylene chloride as a developing solvent to obtain 9.36 g (percent yield 100%) of (R)-2,2'-bis(trifluoromethanesulfonyloxy)-5,5'6,6'7,7'8,8'-octahydro-1,1'-binaphthyl.

(3) Synthesis of (R)-2-diphenylphosphinyl-2'-trifluoromethanesulfonyloxy-5,5'6,6'7,7'8,8'-octahydro- 1,1'-binaphthyl:

In a 50 ml flask were charged 2.68 g (4.80 retool) of (R)-2,2'-bis (trifluoromethanesulfonyloxy) -5,5',6,6',7,7',8,8'-octahydro-1,1'-binaphthyl obtained in (2) above, 1.99 g (9.04 mmol) of diphenylphosphine oxide, and 20 ml of dimethyl sulfoxide in an argon stream to prepare a solution. To the solution were added 108 mg (0.480 mmol) of palladium acetate, 205 mg (0.48 mmol) of 1,4-bis(diphenylphosphino)butane, 5.1 ml of ethyldiisopropylamine, and 33 mg (0,491 mmol) of sodium formate, and the mixture was stirred at room temperature for 20 minutes and then at 90° C. for 19 hours. After cooling to room temperature, 250 ml of ethyl ether and 150 ml of water were added to the reaction mixture, followed by stirring. After separation, the organic layer separated was washed successively with four 125 ml portions of water, two 125 ml portions of 5% diluted hydrochloric acid, two 50 ml portions of water, 125 ml of a saturated sodium hydrogencarbonate aqueous solution, and 125 ml of a saturated sodium chloride aqueous solution. The resulting organic layer was dried over anhydrous magnesium sulfate, and the solvent was removed under reduced pressure. The residue was purified by silica gel column chromatography using toluene/acetonitrile (3:1 by volume) as a developing solution to obtain 2.76 g (percent yield 94%) of the titled compound.

(4) Synthesis of (R)-2-diphenylphosphino-2'-hydroxy-5,5'6,6'7,7'8,8'-octahydro-1,1'-binaphthyl:

In a 50 ml four-necked flask, 318.7 mg (0.664 mmol) of (R)-2-diphenylphosphinyl-2'-trifluoromethanesulfonyloxy-5,5',6,6',7,7',8,8'-octahydro-1,1'-binaphthyl was dissolved in 22 ml of xylene, and 1.21 g (12 mmol) of triethylamine and 1.62 g (12 mmol) of trichlorosilane were added thereto. The reaction mixture was stirred at 120° C. for 17 hours. After cooling the reaction mixture to room temperature, 4.4 ml of a 35% sodium hydroxide aqueous solution was carefully added thereto, followed by stirring for 2 hours. After liquid-liquid separation, the organic layer was washed with two 30 ml portions of a saturated sodium chloride aqueous solution and dried over anhydrous magnesium sulfate. The solvent was removed under reduced pressure. The residue was dissolved in 7 ml of tetrahydrofuran, and a solution of 335 mg (7.98 mmol) of lithium hydroxide in 2.4 ml of water was added thereto, followed by stirring at room temperature for 15 hours. To the reaction mixture were added 50 ml of ethyl ether and 15 ml of 5% diluted hydrochloric acid, followed by separation. The organic layer was washed twice with water and dried over anhydrous magnesium sulfate. The solvent was distilled off, and the residue was purified by silica gel column chromatography using hexane/ethyl acetate (5:1 by volume) as a developing solvent to obtain 105.4 mg (percent yield 51%) of the titled compound.

(5) Synthesis of (S)-1,1'-binaphthalene-2,2'-diyldioxychlorophosphine:

In a 50 ml flask were charged 4.94 g (17.3 mmol) of (S)-1,1'-2-binaphthol and 11.3 g (830 mmol) of phosphorus trichloride in an argon stream, and the mixture was heated at reflux for 4 hours. After cooling to room temperature, the unreacted phosphorus trichloride was removed by distillation under reduced pressure to obtain 5.56 g (percent yield 92%) of the titled compound as a colorless crystal.

(6) Synthesis of (R)-2-diphenylphosphino-5,5',6,6',7,7'8,8'-octahydro-1,1,-binaphthalen-2'-yloxy-((S)-1,1'-binaphthalene- 2,2'-diyldioxy)phosphine:

In a 100 ml flask were charged 0,294 g (0.946 mmol) of (R)-2-diphenylphosphino-2'-hydroxy-5,5'6,6'7,7'8,8'-octahydro-1,1'-binaphthyl, 662 mg (1.89 mmol) of (S)-1,1-binaphthalene-2,2'-diyldioxychlorophosphine, and 30 ml of ethyl ether. To the solution was added 191 mg (1.89 mmol) of triethylamine at 0° C., followed by stirring at room temperature for 15 hours. The reaction was ceased by addition of 20 ml of water. After separation, the organic layer was dried over anhydrous magnesium sulfate, and the solvent was removed under reduced pressure. The residual crude product was purified by silica gel column chromatography using hexane/benzene (1:1 by volume) as a developing solution to obtain 719.4 mg (percent yield 98%) of (R)-2-diphenylphosphino-5,5'6,6'7,7'8,8'-octahydro-1,1'-binaphthalene-2'-yloxy-(S)-1,1'-binaphthalene- 2,2'-diyldioxy)phosphine (hereinafter referred to as (R,S)-OcH-BINAPHOS) as a colorless crystal.

$^{31}$P-NMR (CDCl$_3$) δ: −15.0 (d, J=42.7 Hz), 146.8 (d, J=42.7 Hz)

$^{31}$P-NMR (toluene-d$_8$) δ:

50.4 (dd, H$_{p-p}$=87.0 Hz, J$_{Rh-p}$=174.0 Hz)

160.2 (dd, J$_{Rh-p}$=328.1 Hz)

EXAMPLE 28

Synthesis of (R)-2-Diphenylphosphino-5,5',6,6',7,7',8,8'-octahydro- 1,1'-binaphthalene-2,2'-diyldioxy) phosphine (1) Synthesis of (S)-5,5'6,6'7,7'8,8'-octahydro-1,1'-binaphthalene-2,2'-diyldioxychlorophosphine:

In a 50 ml flask were charged 5.12 g (17.3 mmol) of (S)-5,5',6,6',7,7',8,8'-octahydro-1,1'-bi-2 -naphthol and 11.3 g (830 mmol) of phosphorous trichloride in an argon stream, and the mixture was refluxed for 4 hours. After cooling to room temperature, the unreacted phosphorus trichloride was removed under reduced pressure to obtain 5.7 g (percent yield 92%) of the titled compound as a colorless crystal.

(2) Synthesis of (R)-2-diphenylphosphino-5,5',6,6',7,7',8,8'-octahydro-1,1'-binaphthalen-2'-yloxy-((S)-5,5',6,6',7,7',8,8'-octahydro-1,1'-binaphthalene-2,2'-diyldioxy) phosphine (hereinafter referred to as (R,S)- (OcH)$_2$-BINAPHOS):

(R,S)-(OcH)2-BINAPHOS was obtained in 91% yield in the same manner as in Example 23-(6), except for replacing (S)- 1,1'-binaphthalene-2,2'-diyldioxychlorophosphine as used in Example 23-(6) with (S)-5,5',6,6',7,7',8,8'-octahydro-1,1'-binaphthalene-2,2'-diyldioxychlorophosphine.

$^{31}$P-NMR (CDCl$_3$) δ: −14.7 (d, J=39.7 Hz), 138.3 (d, J=39.7 Hz)

EXAMPLE 29

Synthesis of (R)-2-Diphenylphosphino-1,1'-binaphthalen-2'-yloxy((S)-1,1'-binaphthalene-2,2'-diyldioxy)phosphine (1) Synthesis of (R)-2,2'-bis(trifluoromethanesulfonyloxy)- 1,1'-binaphthyl:

9.56 g of the titled compound was obtained in 100% yield in the same manner as in Example 27-(2), except for replacing (R)-5,5',6,6',7,7',8,8'-octahydro-1,1'-bi-2-naphthol with (R)- 1,1'-bi-2-naphthol.

(2) Synthesis of (R)-2-diphenylphosphinyl-2'-trifluoromethanesulfonyloxy-1,1'-binaphthyl:

2.51 g of the titled compound was obtained in 83% yield in the same manner as in Example 27-(3), except for replacing (R)-2,2'-bis(trifluoromethanesulfonyloxy)-5,5',6,6',7,7',8,8'-octahydro-1,1'-binaphthyl with (R)-2,2'-bis(trifluoromethanesulfonyloxy)-1,1'-binaphthyl.

(3) Synthesis of (R)-2-diphenylphosphino-2'-hydroxy-1,1'-binaphthyl:

153 mg of the titled compound was obtained in 51% yield in the same manner as in Example 27-(4), except for replacing (R)-2-diphenylphosphinyl-2'-hydroxy-5,5',6,6',7,

43

7',8,8'-octahydro-1,1'-binaphthyl with (R)-2-diphenylphosphinyl-2'-hydroxy-1,1'-binaphthyl.

(4) Synthesis of (R)-2-diphenylphosphino-1,1'-binaphthalen-2'-yloxy-((S)-1,1'-binaphthalene-2,2'-diyldioxy)phosphine:

712 mg of the titled compound was obtained in 98% yield in the same manner as in Example 27-(6), except for replacing (R)2-diphenylphosphino-2'-hydroxy-5,5',6,6',7,7',8,8'-octahydro-1,1'-binaphthyl with (R)-2-diphenylphosphino-2'-hydroxy-1,1'-binaphthyl.

EXAMPLE 30

Synthesis of (R)-2-Diphenylphosphino-1,1'-binaphthalen-2'-yloxy-((S)-10,10,-biphenanthrene-9,9'-diyldioxy-)phosphine (1) Synthesis of (S)-10,10'-biphenanthrene-9,9'-diyl-dioxychlorophosphine:

1.05 g of the titled compound was obtained in 90% yield in the same manner as in Example 27-(5), except for replacing (S)-1,1'-bi-2-naphthol with (S)-10,10'-bi-9-phenanthrol.

(2) Synthesis of (R)-2-diphenylphosphino-1,1'-binaphthalen-2,-yloxy-((S)-10,10'-biphenanthrene-9,9'-diyldioxy-)phosphine:

726 mg of the titled compound (hereinafter referred to as (R,S)-phen-binaphos) was obtained in 95% yield in the same manner as in Example 27-(6), except for replacing (S)-1,1'-binaphthalene-2,2'-diyldioxychlorophosphine with (S)-10,10'-biphenanthrene-9,9'-diyldioxychlorophosphine.

$^{31}$P-NMR (C$_6$D$_6$) δ: 148.05 (d, J=21.4 Hz), -13.34 (d, J=21.4 Hz)

EXAMPLE 31

Preparation of Rh(acac)[(S,R)-biphemphos]

In a 20 ml Schlenk tube were charged 39.7 mg (0.05 mmol) of (S,R)-biphemphos of Example 23, 12.8 mg (0.05 mmol) of Rh(acac)$_2$(CO)$_2$ ("acac" represents acetylacetonato, hereinafter the same), and 5 ml of benzene. The solution was stirred at room temperature for 5 minutes, and the solvent was removed under reduced pressure to obtain Rh(acac)[(S,R)-biphemphos] as a yellow solid in 100% yield.

EXAMPLE 32

Preparation of Rh(acac)[(R,R)-biphemphos]

Rh(acac)[(R,R)-biphemphos] was obtained in 100% yield in the same manner as in Example 31, except for replacing (S,R)-biphemphos with (R,R)-biphemphos.

EXAMPLE 33

Preparation of Rh(acac)[(R,S)-Me-biphemphos] and Rh(acac)[(S,S)-biphemphos]

The complexes Rh(acac)[(R,S)-Me-biphemphos] and Rh(acac)[(S,S)-Me-biphemphos] were prepared by the same method of Example 31.

EXAMPLE 34

Preparation of Rh(acac)[(S,R)-H-biphemphos]

Rh(acac)[(S,R)-H-biphemphos] was obtained in 100% yield in the same manner as in Example 31, except for replacing (S,R)-biphemphos with (±,R)-H-biphemphos.

EXAMPLE 35

Preparation of Rh(acac)[(R,S)-OcH-binaphos]

Rh(acac)[(R,S)-OcH-binaphos] was obtained in 100% yield in the same manner as in Example 22, except for replacing (S,R)-biphemphos with (R,S)-OcH-binaphos.

EXAMPLE 36

Preparation of Rh(acac)[(S,R)-OcH-binaphos]

Rh(acac)[(R,S)-OcH-binaphos] was obtained in 100% yield in the same manner as in Example 31, except for replacing (S,R)-biphemphos with (S,R)-OcH-binaphos.

EXAMPLE 37

Preparation of Rh(acac)[(R,S)-(OcH)2-binaphos]

Rh(acac)[(R,S)-(OcH)2-binaphos] was obtained in 100% yield in the same manner as in Example 31, except for replacing (S,R)-biphemphos with (R,S)-(OcH)$_2$-binaphos.

EXAMPLES 38 TO 45

Phosphine compounds shown in Tables 5 and 6 below were prepared in the same manner as in Examples 18 to 23.

EXAMPLES 46 TO 49

Phosphine compound complexes shown in Table 5 below using the phosphine compounds of Examples 42 to 45 were prepared in the same manner as in Examples 31 to 37.

TABLE 5

| Example 38 | Example 39 |
|---|---|
| (S,R)-OcH-BINAPHOS<br>$^{31}$P-NMR δ: | (S,S)-OcH-BINAPHOS<br>$^{31}$P-NMR δ: |

TABLE 5-continued

| | |
|---|---|
| −14.8(d, J=40Hz) | −14.0(br, s) |
| 146.8(d, J=40Hz) | 146.9(d, J=10Hz) |
| Example 40 | Example 41 |
| (S,R)-(OcH)$_2$-BINAPHOS | (S,S)-(OcH)$_2$-BINAPHOS |
| $^{31}$P-NMR δ: | $^{31}$P-NMR δ: |
| −14.6(d, J=41Hz) | −13.4(br, s) |
| 138.2(d, J=39Hz) | 139.1(d, J=8Hz) |

TABLE 6

| | L | |
|---|---|---|
| | Examples 42 and 46 | Examples 43 and 47 |
| | (R)-Ph-binaphos | (R,S)-binaphos |
| | 31P-NMR δ: | 31P-NMR δ: |
| | −10.6(d, J=13.7Hz) | −14.6(d, J=29.0Hz) |
| Metal | 129.2(d, J=13.7Hz) | 144.7(d, J=29.0Hz) |
| Rh | Rh(L)(acac) | (Rh(L)(acac) |
| | 31P-NMR δ: | 31P-NMR δ: |
| | 51.1(dd, J=82.4Hz, J=174.0Hz) | 48.3(dd, J=83.9Hz, J=174.0Hz) |
| | 138.8(dd, J=326.1Hz) | 161.8(dd, J=331.1Hz) |
| | L | |
| | Examples 44 and 48 | Examples 45 and 49 |
| | (R,R)-(OcH)2-binaphos | (R,S)-Me-binaphos |
| | 31P-NMR δ: | 31P-NMR δ: |
| | −18.0(d, J=9.2Hz) | −12.4(d, J=32.0Hz) |
| Metal | 140.5(d, J=9.2Hz) | 145.5(d) |
| Rh | Rh(L)(acac) | (Rh(L)(acac) |
| | 31P-NMR δ: | 31P-NMR δ: |
| | 51.9(dd, J=80.8Hz, J=178.4Hz) | 48.8(dd, J=82.4Hz, J=172.4Hz) |
| | 161.8(dd, J=335.1Hz) | 160.9(dd, J=332.6Hz) |

EXAMPLE 50

Preparation of (S)-(+)-2-Phenylpropanal

In a 50 ml autoclave were charged 38.7 mg (0.0488 mmol) of (S,R)-biphemphos, 3.1 mg (0.012 mmol) of Rh(acac)(CO)$_2$, and a solution of 1250 mg (12.0 mmol) of styrene in 2.4 ml of benzene, and hydrogen and carbon monoxide were fed thereto each to a partial pressure of 50 atm. The mixture was stirred at 60° C. for 42 hours. A conversion of the starting olefin and an aldehyde production ratio were determined by $^1$H-NMR (internal standard: diphenylmethane) analysis, and an optical purity (enantiomer excess) was determined by GLC analysis after conversion of the resulting optically active aldehyde into the corresponding carboxylic acid by Jones oxidation. As a result, the conversion of styrene was 100%, and the 2-phenylpropanal/3-phenylpropanal production ratio was 9:1. The 2-phenylpropanal produced had an optical purity of (S)-(+)-2-phenylpropanal of 94% ee.

EXAMPLES 51 TO 58

Hydroformylation of olefins shown in Table 7 below was carried out in the same manner as in Example 37, except for using the phosphine compound shown in Table 7 and changing the reaction conditions as shown in Table 7. The reaction results obtained are shown in Table 7.

hydrogen and 50 atm of carbon monoxide were fed thereto. The mixture was stirred at 60° C. for 44 hours. The conversion of vinyl acetate was 72%. The product was a mixture comprising 88.6% of 2acetoxypropanal and 11.4% of 3-acetoxypropanal. The optical purity of the 2-acetoxypropanal was 90% ee.

EXAMPLES 60 TO 64

Hydroformylation of styrene or vinyl acetate was carried out in the same manner as in Example 50 or 59, except for using the catalyst or catalyst system shown in Table 8 below and changing the reaction conditions as shown in Table 8. The reaction results obtained are shown in Table 8.

TABLE 7

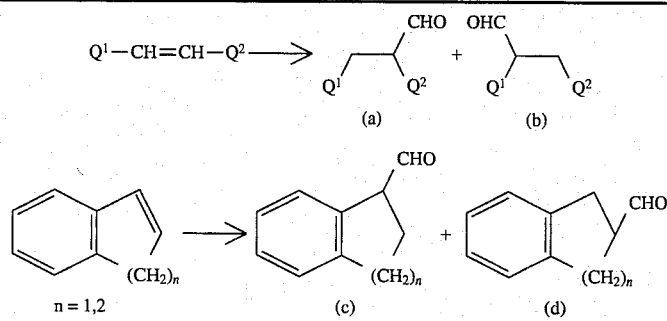

| Example No. | Substrate | Phosphine Compound | Reaction Conditions Temp. (°C.) | Time (hr) | S/C* | Conversion (%) | (a)/(b) or (c)/(d) | Optical Purity of (a) or (c) (% ee) | Absolute Configuration or Specific Rotation |
|---|---|---|---|---|---|---|---|---|---|
| 51 | $Q^1 = H, Q^2 = C_6H_5$ | (R,R)-biphemphos | 60 | 40 | 1000 | 95 | 92/8 | 16 | R-(−) |
| 52 | $Q^1 = H, Q^2 = C_6H_5$ | (S,R)-H-biphemphos + (R,R)-H-biphemphos | 60 | 40 | 1000 | 98 | 89/11 | 69 | S-(+) |
| 53 | $Q^1 = H, Q^2 = OCOCH_3$ | (S,R)-biphemphos | 60 | 40 | 1000 | 65 | 85/15 | 90 | R-(+) |
| 54 | $Q^1 = H, Q^2 = OCOCH_3$ | (R,S)-Me-biphemphos | 60 | 40 | 1000 | 83 | 89/11 | 91 | S-(−) |
| 55 | $Q^1 = H, Q^2 = n\text{-}C_4H_9$ | (S,R)-biphemphos | 30 | 40 | 1000 | 51 | 23/77 | 85 | S-(+) |
| 56 | $Q^1 = Q^2 = CH_3$ | (S,R)-biphemphos | 60 | 40 | 3500 | —** | — | 85 | R-(−) |
| 57 | indene (n = 1) | (S,R)-biphemphos | 60 | 20 | 200 | 62 | 92/8 | 88 | (+) |
| 58 | 1,2-dihydro-naphthalene (n = 2) | (R,S)-biphemphos | 60 | 12 | 500 | 74 | 95/5 | 96 | (−) |

Note:
*S/C is a substrate/rhodium compound ratio
**The conversion of 2-butene was measured per hour because of high volatility of 2-butene As a result, the conversion was 3.7%.

EXAMPLE 59

Preparation of 2-Acetoxypropanal

In a 50 ml autoclave were charged 761 mg (8.84 mmol) of vinyl acetate, 8.6 mg (0.00884 mmol) of Rh(acac)((R,S)-OcH-binaphos), and 8.3 ml of benzene, and 50 atm of

TABLE 8

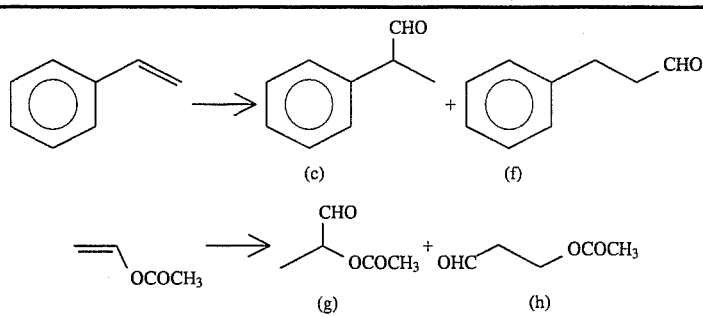

| Example No. | Substrate | Catalyst on Catalyst System | Reaction Conditions Temp. (°C.) | Time (hr) | S/C* | Conversion (%) | (e)/(f) or (g)/(h) | Optical Purity of (e) or (g) (% ee) | Absolute Configuration or Specific Rotation |
|---|---|---|---|---|---|---|---|---|---|
| 60 | styrene | Rh(CO)₂(acac) + (S,R)-binamphos | 60 | 43 | 2056 | 100 | 88/12 | 94 | S-(') |
| 61 | styrene | Rh(S,R)-OcH-binaphos)(acac) | 60 | 100 | 226 | 100 | 93/7 | 93 | |
| 62 | styrene | Rh((R,S)-(OcH)₂-binaphos)(acac) | 60 | 100 | 226 | 84 | 92/8 | 89 | |
| 63 | vinyl acetate | Rh(CO)₂(acac) + (R,S)-binamphos | 60 | 112 | 400 | 98 | 90/10 | 90 | S-(−) |
| 64 | vinyl acetate | Rh((R,R)-binaphos)(acac) | 60 | 37 | 400 | 46 | 92/8 | 73 | S-(−) |

Note:
*S/C is a substrate/rhodium compound ratio.

EXAMPLE 65

Preparation of (R)-2-[(3S,4R)-3-[(R)-1-t-butyldimethylsilyloxyethyl]-2-oxoazetidine-4-yl]propanal In a 100 ml autoclave were charged 9.3 mg (0.01 mmol) of Rh(acac)(R,S)-binaphos, 8 mg (0.01 mmol) of (R,S)-binaphos, and 510 mg (2 mmol) of (1'R,3S,4R)-3-[1'-[(tbu-tyldimethylsilyl)oxy]ethyl]-4-binylazetidine-2-one. After thoroughly purging the autoclave with nitrogen, 5 ml of toluene was added thereto.

Carbon monoxide was introduced into the autoclave under a pressure of 50 atm, and hydrogen was then introduced to a pressure of 100 atm. The mixture was vigorously stirred while heating at 60° C. in an oil bath for 48 hours. After cooling to room temperature, the excess carbon monoxide and hydrogen were released, and toluene was distilled off under reduced pressure. Purification of the residue by silica gel column chromatography afforded 513 mg (90%) of a 94:6 mixture of (R)- 2-[(3S,4R)-3-[(R)-1-t-butyldimethylsilyloxyethyl]-2 -oxoazetidine-4-yl]propanal.

The 2(R)/2(S) ratio was decided from the integrated ratio and aldehyde proton by ¹H-NMR. Further, the product as obtained was subjected to Jones oxidation to the corresponding mixed carboxylic acid. The resulting mixture was analyzed by high-performance liquid chromatography (Inertsil ODS-2; eluent: acetonitrile/water=6:4; pH=2.3 ($H_3PO_4$)), and the results obtained were compared with those of a standard sample.

2 (R)-Isomer:
¹H-NMR (CDCl₃) δ:
0.07 (s,3H), 0.08 (s,3H), 0.88 (s,9H), 1.22 (d, J=7.3 Hz, 3H), 1.24 (d, J=6.3 Hz, 3H), 2.68 (m, 1H), 3.94 (dd, J=5.4, 2.4 Hz, 1H), 4.20 (m, 1H), 5.98 (s,1H), 9.81 (J=1.01 Hz)

EXAMPLES 66 TO 72

A (2R/2S)-mixed formylated compound was obtained in the same method as in Example 65 except for using the catalyst or precursor shown in Table 9 below.

TABLE 9

| Example No. | Catalyst | 2R/2S | Yield (%) |
|---|---|---|---|
| 66 | [Rh(COD)Cl]₂ + (R,S)-binaphos | 94/6 | 89 |
| 67 | Rh(acac)((R,S)-OcH-binaphos | 94/6 | 70 |
| 68 | [Rh(COD)Cl]₂ + (R,S)-(OcH)₂-binaphos | 65/35 | 65 |
| 69 | Rh(acac)((R,S)-bin-OcH-binaphos)* | 52/48 | 70 |
| 70 | Rh(CO)₂(acac) + (R,S)-biphemphos | 93/7 | 75 |
| 71 | Rh(CO)₂(acac) + (R,S)-phen-binaphos | 95/5 | 70 |
| 72 | Rh(CO)₂(acac) + (R,S)-Me₂-binaphos** | 92/8 | 40 |

*(R)-2-diphenylphosphino-1,1'-binaphthalene-2'-yloxy-((S)-5,5',6,6',7,7',8,8'-octahydro-1,1'-binaphthalene-2,2'-diyldioxy)phosphine
**(R)-2-diphenylphosphino-1,1'-binaphthalene-2'-yloxy-((S)-3,3'-dimethyl-1,1'-binaphthalene-2,2'-diyldioxy)phosphine

EXAMPLES 73 TO 75

A (2R/2S)-mixed formylated compound was obtained in the same method as in Example 65, except for using the solvent shown in Table 10 below.

TABLE 10

| Example No. | Solvent | 2R/2S | Yield (%) |
|---|---|---|---|
| 73 | benzene | 94/6 | 90 |
| 74 | dimethoxyethane | 84/16 | 62 |
| 75 | ethyl acetate | 78/22 | 89 |

According to the present invention, optically active aldehydes can be obtained with high regio and enantio selectivities by hydroformylation of olefins in the presence of a combination of the specific phosphine compound according to the present invention and a transition metal compound or in the presence of a complex prepared from the phosphine compound and the transition metal compound.

While the invention has been described in detail and with reference to the specific examples thereof, it will be apparent to one skilled in the art that various changes and modifications can be made therein without departing from the spirit and scope thereof.

What is claimed as new and desired to be secured by Letters Patent of the United States is:

1. A phosphine compound represented by the following formula (1):

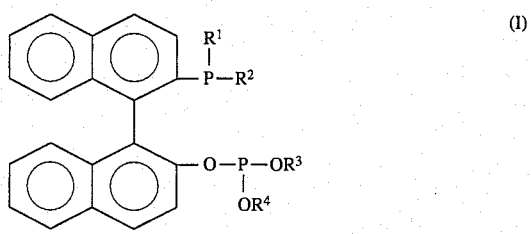

wherein $R^1$ and $R^2$ are identical with or different from each other and mean individually a phenyl group which may be substituted by a halogen atom or lower alkyl group, or denote together a divalent hydrocarbon group, $R^3$ and $R^4$ are identical with or different from each other and mean individually a lower alkyl group or a phenyl group which may be substituted by a halogen atom, lower alkyl group or lower alkoxy group, or denote together a divalent hydrocarbon group.

2. A transition metal-phosphine complex containing of a transition metal selected from the group consisting of rhodium, ruthenium, palladium, iridium, platinum, cobalt, nickel and titanium and as a ligand, the phosphine compound according to claim 1.

3. A rhodium-phosphine complex represented by the following formula (2-a) or (2-b):

[Rh(L) (Y) (X)]   (2-a)

[Rh(L) (Y) ](X)   (2-b)

wherein L means the phosphine compound according to claim 1, Y denotes carbon monoxide, a monodentate or bidentate neutral ligand having lower coordinating strength than that of carbon monoxide, olefin or diene, and X stands for a hydrogen atom, monovalent anion or triphenylphosphine, or X and Y means together a β-diketonate.

4. The rhodium-phosphine complex according to claim 3, wherein in the formula (2-a) or (2-b), the combination of X and Y is selected from the group consisting of the following combinations:

(a) Y=CO and X=halogen atom or cyano group;

(b) Y=cycloocta-1,5-diene and X=halogen atom, $ClO_4$, $BF_4$, $PF_6$, $CH_3COO$ or cyano group;

(c) Y=norbornadiene and X=halogen atom, $ClO_4$, $BF_4$, $PF_6$, $CH_3COO$ or cyano group;

(d) Y=$(CO)_2$ and X=hydrogen atom or (triphenylphosphine)$_2$;

(e) Y=$(CO)_3$ and X=triphenylphosphine;

(f) Y=ethylene and X=halogen atom or cyano group;

(g) Y=pyridine and X=chlorine or bromine atom; and (h) X and Y=together β-diketonate.

5. A phosphine compound represented by formula (II):

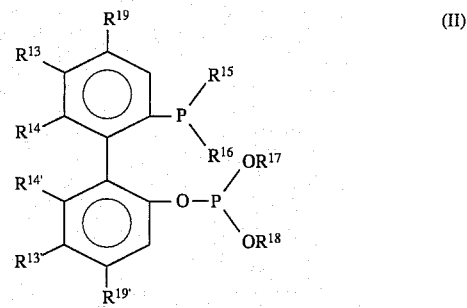

wherein $R^{14}$ and $R^{14'}$, which may be the same or different, each represent a hydrogen atom, a lower alkyl group or a lower alkoxy group; $R^{13}$, $R^{13'}$, $R^{19}$ and $R^{19'}$ which may be the same or different, each represent a hydrogen atom, a lower alkyl group, a lower alkoxy group or a halogen atom; $R^{15}$ and $R^{16}$, which may be the same or different, each represent a phenyl group or a phenyl group substituted with a lower alkyl group, a halogen atom or a lower alkoxy group; and $R^{17}$ and $R^{18}$, which may be the same or different, each represent a phenyl group or a phenyl group substituted with a lower alkyl group, a lower alkoxy group or a halogen atom; or $R^{17}$ and $R^{18}$ may be taken together to form a divalent hydrocarbon group.

6. A transition metal phosphine complex composed of a transition metal selected from rhodium, ruthenium, iridium and platinum and a phosphine compound represented by formula (VIII):

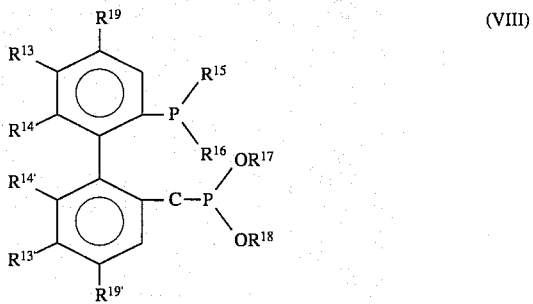

wherein $R^{14}$ and $R^{14'}$, which may be the same or different, each represent a hydrogen atom, a lower alkyl group or a lower alkoxy group; $R^{13}$, $R^{13'}$, $R^{19}$, and $R^{19'}$, which may be the same or different, each represent a hydrogen atom, a lower alkyl group, a lower alkoxy group or a halogen atom; $R^{15}$ and $R^{16}$, which may be the same or different, each represent a phenyl group or a phenyl group substituted with a lower alkyl group, a halogen atom or a lower alkoxy group; and $R^{17}$ and $R^{18}$, which may be the same or different, each represent a phenyl group or a phenyl group substituted with a lower alkyl group, a lower alkoxy group or a halogen atom; or $R^{17}$ and $R^{18}$ may be taken together to form a divalent hydrocarbon group, as a ligand.

7. A process for producing an optically active aldehyde comprising hydroformylation of an olefin represented by formula (IX):

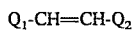 (IX)

wherein Q₁ represents a hydrogen atom or a lower alkyl group; and Q₂ represents a lower alkyl group, a lower alkoxy group, a halogen atom, a lower alkylcarbonyloxy group, a cyano group, a carboxyl group, a lower alkylcarbonyl group, a lower alkoxycarbonyl group, a phthalimido group, an acetylamino group, a benzoylamino group, a mono-lower alkylamino group, a di-lower alkylamino group, a benzoyl group, a phenyl group, a naphthyl group, a phenyl or naphthyl group substituted with a lower alkyl group, a lower alkoxy group or a halogen atom, or a group represented by formula (X):

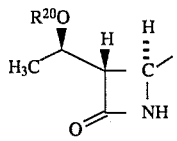 (X)

wherein R²⁰ represents a hydrogen atom or a hydroxyl-protecting group;

or Q1 and Q2 may be taken together to form a ring represented by formula (XI):

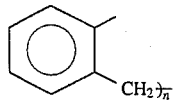 (XI)

wherein n represents 1 or 2, in the presence of both (1) a compound of a transition metal selected from the group consisting of rhodium, ruthenium, iridium and platinum and (2) a phosphine compound represented by formula (VIII):

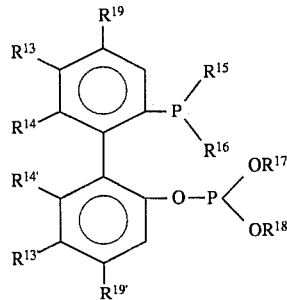 (VIII)

wherein R¹⁴ and R¹⁴' which may be the same or different, each represent a hydrogen atom, a lower alkyl group or a lower alkoxy group; R¹³, R¹³', R¹⁹ and R¹⁹', which may be the same or different, each represent a hydrogen atom, a lower alkyl group, a lower alkoxy group or a halogen atom; R¹⁵ and R¹⁶, which may be the same or different, each represent a phenyl group or a phenyl group substituted with a lower alkyl group, a halogen atom or a lower alkoxy group; and R¹⁷ and R¹⁸, which may be the same or different, each represent a phenyl group or a phenyl group substituted with a lower alkyl group, a lower alkoxy group or a halogen atom; or R¹⁷ and R¹⁸ may be taken together to form a divalent hydrocarbon group, or (3) a previously prepared complex composed of compounds (1) and (2).

8. A process for producing an optically active aldehyde comprising hydroformylation of an olefin represented by formula (IX):

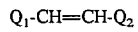 (IX)

wherein Q₁ represents a hydrogen atom or a lower alkyl group; and Q₂ represents a lower alkyl group, a lower alkoxy group, a halogen atom, a lower alkylcarbonyloxy group, a cyano group, a carboxyl group, a lower alkylcarbonyl group, a lower alkoxycarbonyl group, a phthalimido group, an acetylamino group, a benzoylamino group, a mono-lower alkylamino group, a di-lower alkylamino group, a benzoyl group, a phenyl group, a naphthyl group, a phenyl or naphthyl group substituted with a lower alkyl group, a lower alkoxy group or a halogen atom, or Q₁ and Q₂ may be taken together to form a ring represented by formula (XI):

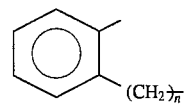 (XI)

wherein n represents 1 or 2, in the presence of both (1) a compound of a transition metal selected from the group consisting of rhodium, ruthenium, iridium and platinum and (2) a phosphine compound represented by formula (I):

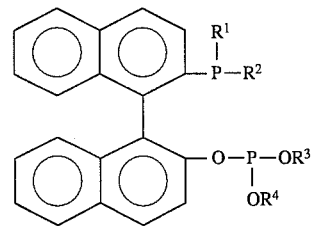 (I)

wherein R¹ and R² are identical with or different from each other and mean individually a phenyl group which may be substituted by a halogen atom or lower alkyl group, or denote together a divalent hydrocarbon group, R³ and R⁴ are identical with or different from each other and mean individually a lower alkyl group or a phenyl group which may be substituted by a halogen atom, lower alkyl group or lower alkoxy group, or denote together a divalent hydrocarbon group, or (3) a previously prepared complex composed of compounds (1) and (2).

9. The process according to claim 8, wherein the complex is a rhodium-phosphine complex represented by the following formula (3-a) or (3-b):

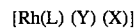 [Rh(L) (Y) (X)]   (3-a)

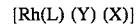 [Rh(L) (Y) (X)]   (3-b)

wherein L means a phosphine compound represented by the following formula:

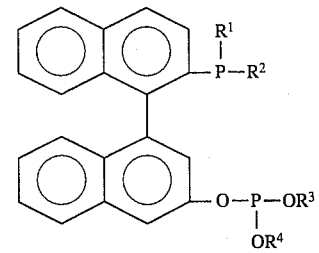 (I)

wherein R¹ and R² are identical with or different from each other and mean individually a phenyl group which may be substituted by a halogen atom or lower alkyl group, or denote together a divalent hydrocarbon group, R³ and R⁴ are identical with or different from each other and mean individually a lower alkyl group or a phenyl group which may be substituted by a halogen atom, lower alkyl group or lower alkoxy group, or denote together a divalent hydrocarbon group, Y denotes carbon monoxide, a monodentate or bidentate neutral ligand having lower coordinating strength than that of carbon monoxide, olefin or diene, and X stands for a hydrogen atom, monovalent anion or triphenylphosphine, or X and Y mean together a β-diketonate.

10. The process according to claim 9, wherein the vinyl compound is selected from the group consisting of vinyl acetate, N-vinylphthalimide, vinyl chloride, styrene, acrylonitrile, 4-isobutylstyrene and 2-methoxy-6-vinylnaphthalene.

11. The process according to claim 9, wherein the binaphthyl skeleton of the phosphine compound in the formula (3-a) or (3-b) has an optically active R or S structure.

* * * * *

UNITED STATES PATENT AND TRADEMARK OFFICE
CERTIFICATE OF CORRECTION

PATENT NO. : 5,530,150
DATED : June 25, 1996
INVENTOR(S) : Hidemasa TAKAYA, et al.

It is certified that error appears in the above-identified patent and that said Letters Patent is hereby corrected as shown below:

Column 2, line 12, "have been not" should read --have not been--.

Column 5, line 28, "[Rh (L) (Y) (X)" should read --[Rh (L) (Y)] (X)--.

Column 12, line 14, "corresponding t" should read --corresponding to--.

Column 13, line 63, "8,8" should read --8,8'--.

Column 18, line 41, "10" should read --10--.
         line 43, "binaphthYl" should read --binaphthyl--.
         line 43, "11" should read --11--.
         line 46, "12" should read --12--.
         line 49, "13" should read --13--.
         line 50, "13" should read --13--.
         line 51, "14" should read --14--.
         line 52, "15" should read --15--.

Column 19, line 62, "$3_1$p-NMR" should read --$^{31}$P-NMR--.

Column 21, line 17, "not" should read --no--.
         line 19, "0,001" should read --0.001--.
         line 33, "aidehyde" should read --aldehyde--.
         line 45, insert --(XII):-- after formula.

Column 22, line 39, "phosphinte" should read --phosphine--.

UNITED STATES PATENT AND TRADEMARK OFFICE
CERTIFICATE OF CORRECTION

PATENT NO. : 5,530,150
DATED : June 25, 1996
INVENTOR(S) : Hidemasa TAKAYA, et al.

It is certified that error appears in the above-identified patent and that said Letters Patent is hereby corrected as shown below:

Column 23, line 43, both occurrences, "(0,491 mmol)" should read
--(0.491 mmol)--.
line 45, "(0,491 mmol)" should read --(0.491 mmol)--.
line 51, "andan" should read --and an--.
line 59, "o#" should read --of--.
line 65, "0,664 mmol" should read --0.664 mmol--.

Column 24, line 37 "0,946 mmol" should --0.946 mmol--.

Column 25, line 2, delete "triethylamine".
line 44, "0,025 mmol" should read --0.025 mmol--.
line 46, "0,025 ml" should read --0.025 ml--.

Column 26, line 25, "1,301 g" should read --1.301 g--.

Column 27, line 10, "1,273 g" should read --1.273 g--.
line 20, "1,1'-binaphthalen" should read --1,1'-binaphthalene--.
line 64, "0,491 mmol" should read --0.491 mmol--.

Column 28, line 33, "mE" should read --ml--.
line 54, "0,946 mmol" should read --0.946 mmol--.
line 55, "dihenylphosphino" should read
--diphenylphosphino--.

UNITED STATES PATENT AND TRADEMARK OFFICE
CERTIFICATE OF CORRECTION

PATENT NO. : 5,530,150
DATED : June 25, 1996
INVENTOR(S) : Hidemasa TAKAYA, et al.

Page 3 of 6

It is certified that error appears in the above-identified patent and that said Letters Patent is hereby corrected as shown below:

Column 29, line 1, "binaphthalen" should read --binaphthalene--.
    line 4, "$^{31}$p-NMR" should read --$^{31}$P-NMR)--.
    line 10, "binaphthalen" should read --binaphthalene--.
    line 12, "5, 5' 6, 6, 7, 7', 8, 8'" should read --5, 5', 6, 6', 7, 7', 8, 8'--.
    line 23, "binaphthalen" should read --binaphthalene--.
    line 31, "$^{31}$p-NMR" should read --$^{31}$P-NMR--.

Column 30, line 9, "SINAPHOS" should read --BINAPHOS--.

Column 32, line 39, "(0,491 mmol)" should read --(0.491 mmol)--.
    line 40, "(0,491 mmol)" should read --(0.491 mmol)--.
    line 42, "(0,491 mmol)" should read --(0.491 mmol)--.
    line 60, "-1.1'" should read --1,1'--.

Column 33, line 23, "0.83 mol" should read --0.83 mmol--.
    line 31, "-1.1'" should read --1,1'--.
    line 46, "$^{31}$p-NMR" should read --$^{31}$P-NMR--.
    line 49, "1,301 g" should read --1.301 g--.

Column 34, line 16, "$^{31}$p-NMR" should read --$^{31}$P-NMR--.
    line 27, "$^{31}$p-NMR" should read --$^{31}$P-NMR--.
    line 27, "(dd, J$^{p-p}$" should read --(dd, J$_{p-p}$--.
    line 40, "(S)-)(-)-2" should read --(S)-(-)-2--.

Column 35, line 57, "of in" should read --1N--.

UNITED STATES PATENT AND TRADEMARK OFFICE
CERTIFICATE OF CORRECTION

PATENT NO. : 5,530,150
DATED : June 25, 1996
INVENTOR(S) : Hidemasa TAKAYA, et al.

It is certified that error appears in the above-identified patent and that said Letters Patent is hereby corrected as shown below:

Column 36, line 4, "(20.0 mol)" should read --(20.0 mmol)--.

Column 37, line 65, "(3.81)mmol)" should read --(3.81 mmol)--.

Column 38, line 12, "$_D^8$" should read --$_D^2$--.
        line 38, "273°" should read --$\alpha_D^2$: 273°
        line 56, "(±)-2, 2', 3 3', 4, 4'" should read --(±)-2, 2', 3, 3', 4, 4'--

Column 39, line 37, "(d, $H_{p-p}$=39.6 Hz) should read --(d, $J_{p-p}$ =39.6 Hz)--.
        line 41, "(d, $H_{p-p}$=13.8 Hz)" should read --(d, $J_{p-p}$=13.8 Hz)--.

Column 40, line 21, "(d, $H_{p-p}$=35.1 Hz)" should read --(d, $J_{p-p}$=35.1 Hz)--.
        line 24, "(d,$H_{p-p}$=21.4 Hz)" should read --(d, $J_{p-p}$=21.4 Hz)--.
        line 30, "binaphthalen" should read --binaphthalene--.
        line 51, "(52.2 retool)" should read --(52.2 mmol)--.
        line 52, "(7.83 retool) should read --(7.83 mmol)--.
        line 60, "7' 8" should read --7', 8--.
        line 61, "5, 5'6, 6'7, 7'8, 8'" should read --5, 5', 6, 6', 7, 7', 8, 8'--.
        line 64, "5' 6" should read --5', 6--.
        line 66, "(4.80 retool)" should read --(4.80 mmol)--.

UNITED STATES PATENT AND TRADEMARK OFFICE
CERTIFICATE OF CORRECTION

PATENT NO. : 5,530,150
DATED : June 25, 1996
INVENTOR(S) : Hidemasa TAKAYA, et al.

It is certified that error appears in the above-identified patent and that said Letters Patent is hereby corrected as shown below:

Column 41, line 7, "(0,491 mmol)" should read --(0.491 mmol)--.
line 60, "8'-octahydro-1,1" should read --8'-octahydro-1, 1'--.
line 62, "0,294g" should read --0.294g--.
line 63, "5, 5' 6, 6' 7, 7' 8, 8'" should read --5', 6, 6', 7, 7', 8, 8'--.
line 64, "(S) - 1, 1" should read --(S) - 1, 1'--.

Column 42, line 8, "5, 5' 6, 6' 7, 7' 8, 8'" should read --5, 5', 6, 6', 7, 7', 8, 8'--.
line 15, "(dd, $H_{p-p}$" should read --(dd, $J_{p-p}$--.
line 21, "octahydro- 1,1'-binaphthalene-2,2'-diyldioxy) phosphine" should read --octahydro-1, 1'-binaphthalen-2'-yloxy- ((S) -5, 5', 6, 6', 7, 7', 8, 8'-octahydro-1, 1'-binaphthalene-2, 2'-diyldioxy) phosphine--.
line 22, "5, 5' 6, 6' 7, 7' 8, 8'" should read --5, 5', 6, 6', 7, 7', 8, 8'--.
line 33, "binaphthalen" should read --binaphthalene--.
line 38, "1,1" should read --1, 1'--.
lines 46 and 47, "binaphthalen" should read --binaphthalene--.

Column 43, lines 3 and 4, "binaphthalen" should read --binaphthalene--.
lines 14 and 15, "binaphthalen" should read --binaphthalene--.

UNITED STATES PATENT AND TRADEMARK OFFICE
CERTIFICATE OF CORRECTION

PATENT NO. : 5,530,150
DATED : June 25, 1996
INVENTOR(S) : Hidemasa TAKAYA, et al.

It is certified that error appears in the above-identified patent and that said Letters Patent is hereby corrected as shown below:

Column 43, lines 23 and 24, "binaphthalen" should read -- binaphthalene--.

Column 48, line 4, "2acetoxypropanal" should read -- 2-acetoxypropanal--.

Columns 49 and 50, TABLE 8, column 3, Examples 60 and 63 "binamphos" should read --binaphos--.
line 41, "[(tbu-" should read --[(t-bu---.

Column 54, line 44, "[Rh(L) (Y)(X)]" should read --[Rh(L) (Y)] (X)--.

Signed and Sealed this

Eighteenth Day of August, 1998

*Attest:*

BRUCE LEHMAN

*Attesting Officer*          *Commissioner of Patents and Trademarks*